(12) United States Patent
Shirasaki et al.

(10) Patent No.: US 11,041,848 B2
(45) Date of Patent: Jun. 22, 2021

(54) METHOD AND SYSTEM FOR CELL COLLECTION BASED ON INFORMATION REGARDING CHANGE OVER TIME

(71) Applicant: THE UNIVERSITY OF TOKYO, Tokyo (JP)

(72) Inventors: Yoshitaka Shirasaki, Tokyo (JP); Sotaro Uemura, Tokyo (JP); Yumiko Tanaka, Tokyo (JP); Mai Shirasaki, Tokyo (JP)

(73) Assignee: The University of Tokyo, Tokyo (JP)

( * ) Notice: Subject to any disclaimer, the term of this patent is extended or adjusted under 35 U.S.C. 154(b) by 357 days.

(21) Appl. No.: 16/070,999

(22) PCT Filed: Jan. 19, 2017

(86) PCT No.: PCT/JP2017/001770
§ 371 (c)(1),
(2) Date: Dec. 12, 2018

(87) PCT Pub. No.: WO2017/126615
PCT Pub. Date: Jul. 27, 2017

(65) Prior Publication Data
US 2019/0120826 A1 Apr. 25, 2019

(30) Foreign Application Priority Data
Jan. 19, 2016 (JP) .............................. JP2016-007715

(51) Int. Cl.
*G01N 33/50* (2006.01)
*C12M 1/00* (2006.01)
*C12M 1/26* (2006.01)
*G01N 33/569* (2006.01)
*G01N 33/68* (2006.01)
*G01N 21/64* (2006.01)

(52) U.S. Cl.
CPC .......... *G01N 33/5041* (2013.01); *C12M 1/26* (2013.01); *C12M 47/04* (2013.01); *G01N 33/56966* (2013.01); *G01N 33/6869* (2013.01); *G01N 21/6408* (2013.01); *G01N 2333/5437* (2013.01)

(58) Field of Classification Search
None
See application file for complete search history.

(56) References Cited

PUBLICATIONS

Shirasaki et al., Real-time single-cell imaging of protein secretion, Scientific Reports, 4: 4736; pp. 1-7, published Apr. 22, 2014. (Year: 2014).*

* cited by examiner

*Primary Examiner* — Rebecca M Giere
(74) *Attorney, Agent, or Firm* — W&C IP

(57) ABSTRACT

There is provided a method that can recover a cell having specific cell information, of cells having cell information that changes over time, from a cell group. A cell recovery method for recovering a specific cell from a cell group including a plurality of cells having cell information that changes over time includes (a) a step of detecting or measuring a desired indicator in each cell of the cell group along a time axis, and (b) a step of recovering a cell having undergone a predetermined change in the indicator, wherein the cell is recovered at a time point after elapse of a preset time since a time point of occurrence of a predetermined change in the indicator.

12 Claims, 14 Drawing Sheets

Negative : At least one of N1 to N4 exhibits FPKM > 100
Positive: At least one of P1 to P3 exhibits FPKM > 100
Real-time: R1 exhibits FPKM > 100 iPS (I-1-5)

<Original>

<Segmentation>
Original
↓ Background subtraction
↓ Detect Peak
↓ Low Pass filter
↓ Thresholding
Object segmentation <Feature extraction>
Original
↓ Background subtraction
↓ Edges Detection
↓ Measure in objects
Feature intensities

METHOD AND SYSTEM FOR CELL COLLECTION BASED ON INFORMATION REGARDING CHANGE OVER TIME

TECHNICAL FIELD

The present invention relates to a method and system for recovering cells based on information that changes over time.

BACKGROUND ART

Cell information includes genetic DNA-sequence information (genome), epigenetic information (epigenome) that controls the expression of genes, gene primary transcript (for example, mRNA) information (transcriptome), modification information (proteome) concerning the translation volume, phosphorylation, oxidation, glycosylation, and the like of proteins, and metabolite information (metabolome). It is known that genome and epigenome are comparatively stable information with respect to the elapse of time, but information such as transcriptome and proteome sometimes fluctuates in minutes (Non-Patent Literature 1). On the other hand, it is known that even if external stimuli are uniformly applied to all cells, their state changes do not always shift at the same timing among them, and the start time points of change differ among the respective cells (Non-Patent Literature 2).

Conventionally, specimens used for the analysis of cell information generally included a cell group collectively recovered at the end point of measurement after the elapse of a predetermined time since the application of external stimuli. Information about cells contained in a specimen subjected to bulk analysis might vary among the respective cells, especially with regard to cell information fluctuating on a minute-by-minute basis. In analyses on information that changes on a minute-by-minute basis, such as transcriptome and proteome in particular, most of the cell information becomes obscure when information of the respective cells is simply integrated from all the cells with ignoring the timing variation.

Therefore, in order to examine or use cell information that changes, for example, on a minute-by-minute basis, it is desired to obtain time progress information starting from a change in indicator as well as recovering cells on a cell-by-cell based on a change in each cell indicator.

FOR EXAMPLE, A FLOW CYTOMETRY/CELL SORTER HAS BEEN KNOWN AS A METHOD FOR RECOVERING SPECIFIC CELLS FROM MANY CELLS BASED ON THE SHIFT OF A SPECIFIC INDICATOR OF CELLS. IN THIS METHOD, SPECIFIC INDICATORS IN EACH CELL ARE OPTICALLY ANALYZED BY FLOW CYTOMETRY AND CELLS ARE SORTED BY USING A CELL SORTER BASED ON THE RESULTS OF THE INDICATOR ANALYSIS. HOWEVER, THIS TECHNIQUE PROVIDES NO TIME-DEPENDENT INFORMATION WITH RESPECT TO CHANGES IN INDICATOR.

ALSO, A SINGLE CELL PICKING TECHNIQUE HAS BEEN KNOWN AS A METHOD FOR RECOVERING SPECIFIC CELLS FROM MANY CELLS BASED ON THE SHIFT OF A SPECIFIC INDICATOR OF CELLS. THIS TECHNIQUE IS DESIGNED TO SPECIFY TARGET CELLS AMONG MANY CELL GROUPS BASED ON FLUORESCENCE INTENSITY AND IMAGE INFORMATION AND RECOVER THE TARGET CELLS ON A CELL-BY-CELL BASIS BY MICROCAPILLARY. HOWEVER, THIS METHOD CANNOT ALSO OBTAIN ANY TIME-DEPENDENT INFORMATION WITH RESPECT TO CHANGES IN INDICATOR. CITATION LIST

NON-PATENT LITERATURE

Non-Patent Literature 1: Coulon A. et al., "Eukaryotic transcriptional dynamics: from single molecules to cell populations." Nature Reviews Genetics (2013) 14, 572-584

Non-Patent Literature 2: Liu T. et al., "Single-cell imaging of caspase-1 dynamics reveals an all-or-none inflammasome signaling response." Cell Rep. (2014) 8(4): 974-982

Non-Patent Literature 3: Shirasaki Y. et al., "Real-time single-cell imaging of protein secretion." Scientific reports (2014) 4:4736; DOI: 10.1038/srep04736

SUMMARY OF THE INVENTION

Problems to be Solved by the Invention

In consideration of the above problem, the present invention provides a cell recovery method that obtains cell information changing in chronological order in, for example, minutes, which has been obscured by conventional cell recovery methods, and can recover cells having specific cell information from a cell group.

Means for Solving the Problem

In order to accurately know the internal states of cells that change from moment to moment without being influenced by variations in the start point of reaction of the respective cells, it is necessary to perform real-time detection of the time point of change in indicator representing the cell state of "each cell" with a high time resolution, for example, on a minute-by-minute basis, real-time recovery after the elapse of a preset time $\Delta t$ for instantaneous stoppage of the time transition of cell information with a time resolution, for example, on a minute-by-minute basis, and quantitative analysis of intracellular information on a cell-by-cell basis.

Note that as a technique of observing cell information that changes, for example, on a minute-by-minute basis, a live cell imaging technique of measuring a specific indicator for each cell has been reported. For example, Non-Patent Literature 3 discloses a single-cell secretion imaging technique of monitoring on a minute-by-minute basis for each cell to see how monocytes secrete cytokines upon application of external stimuli.

The present inventors have conceived a technique of recovering cells (real-time recovery) in a specific state at a time point ($\Delta t$) after the elapse of a preset time since the time point of a change in a specific indicator with a time resolution, for example, on a minute-by-minute basis as an application of live cell imaging technology.

Along to the above idea, the present inventors actually measured the interleukin-13-secretion response (the upper case letters "IL" represent an interleukin protein, hereinafter) of mouse group 2 innate lymphoid cells (mouse natural helper cells: mouse NH cells) against the stimulus of IL-33 or IL-2/IL-25. The present inventors then recovered mouse group 2 innate lymphoid cells on a cell-by-cell basis at a time point after the elapse of a preset time ($\Delta t$) since the start point of secretion response. As a result, the present inventors newly found that an Il13 mRNA expression pattern took a dynamic gene expression or static gene expression depending on IL-33 or IL-2/IL-25 stimulus. This indicates that the method according to the present invention can find cell information that has been obscured by the conventional collective recovery technique at the end point of measurement.

That is, the present invention provides the following method.

According to an aspect of one embodiment, the present invention relates to

[1] a cell recovery method for recovering a specific cell from a cell group including a plurality of cells having cell information that changes over time, including:

(a) a step of detecting or measuring a desired indicator in each cell of the cell group along a time axis; and (b) a step of recovering a cell having undergone a predetermined change in the indicator, wherein the cell is recovered at a time point after elapse of a preset time since a time point of occurrence of a predetermined change in the indicator.

According to one embodiment, in the method of the present invention,

[2] the method described in [1] further includes, after the step (a) and before the step (b), (i) a step of comparing a detected value or a measured value obtained in the step (a) with a preset threshold and determining the cell as a cell to be recovered from the cell group based on the exceeding the threshold in the value of the cell which is determined for a cell having undergone a predetermined change in the indicator. According to one embodiment, in the method of the present invention,

[3] the method described in [1] or [2] further includes, after the step (a) and before the step (b), (ii) a step of comparing a detected value or a measured value having time axis information obtained in the step (a) with a preset threshold to specify a time point when the threshold is exceeded, and determining the specified time point as a time point of occurrence of a predetermined change in the indicator.

According to one embodiment, in the method of the present invention,

[4] the method described in [3] further includes, after the step (b), (c) a step of correcting a time point of occurrence of a predetermined change in the indicator based on information of the chronologically obtained indicator with respect to a recovered cell, and calculating an elapsed time from the corrected time point of occurrence of the predetermined change in the indicator to a time point of recovery of the cell.

According to one embodiment, in the method of the present invention,

[5] in the method described in any one of [1] to [4], the recovery of the cell in the step (b) is recovery on a cell-by-cell basis.

According to one embodiment, in the method of the present invention,

[6] in the method described in any one of [1] to [5], each of the steps is performed on an array chip including a plurality of wells each containing one cell.

According to one embodiment, in the method of the present invention,

[7] in the method according to any one of [1] to [6], the step (a) and the step (b) are repeated multiple times to recover a plurality of specific cells.

According to one embodiment, in the method of the present invention,

[8] in the method described in [7], not less than two different times each are set as the preset time to recover specific cells indifferent states as not less than two groups.

According to one embodiment, in the method of the present invention,

[9] in the method according to any one of [1] to [8], the step (b) includes a step of fixing a cell at a time point after elapse of a preset time since a time point of occurrence of a predetermined change in the indicator and recovering the fixed cell.

According to one embodiment, in the method of the present invention,

[10] in the method described in any one of [1] to [9], the step (b) includes a step of transporting the recovered cell to a fixative solution or a culture solution.

According to one embodiment, in the method of the present invention,

[11] in the method described in any one of [1] to [10], the indicator includes a secreted protein from a cell and detection or measurement of the indicator is performed by a sandwich immunoassay using the evanescent light as an excitation light generated only near a well bottom surface.

According to another aspect of one embodiment, the present invention relates to

[12] a method for processing a cell recovered by a method described in any one of [1] to [11] for cell information analysis, wherein the step (b) in the method described in any one of [1] to [11] includes a step of transporting a cell in a culture solution into purified water or inorganic saline solution, and recovering the cell together with the culture solution such that a ratio of the culture solution to whole purified water or whole inorganic saline solution becomes not more than 20% (v/v), and the method further includes a step of fixing a recovered cell in the purified water or the inorganic saline solution.

According to still another aspect of one embodiment, the present invention relates to

[13] a cell analysis method including a step of analyzing cell information of a cell recovered by a method described in one of [1] to [12].

According to still another aspect of one embodiment, the present invention relates to

[14] a system for recovering a specific cell from a cell group including a plurality of cells having cell information that changes over time, wherein a desired indicator in each cell of the cell group is detected or measured by a detection unit along a time axis, an analyzing unit specifies a cell having undergone a predetermined change in the indicator, a time point of occurrence of the predetermined change in the indicator, and a time point after elapse of a preset time since a time point of occurrence of the predetermined change in the indicator, and a recovering unit recovers a cell having undergone the predetermined change in the indicator at a time point after elapse of a preset time since a time point of occurrence of the predetermined change in the indicator.

Note that the cell recovery method according to the present invention can be regarded as a cell preparation method.

That is, the present invention provides

[1'] a cell preparation method for preparing a specific cell from a cell group including a plurality of cells having cell information that changes over time, including:

(a) a step of detecting or measuring a desired indicator in each cell of the cell group along a time axis; and (b) a step of recovering a cell having undergone a predetermined change in the indicator, wherein the cell is recovered at a time point after elapse of a preset time since a time point of occurrence of a predetermined change in the indicator.

According to the cell preparation method described in [1'], there is also provided a preparation method including one feature or a combination of a plurality of features in the cell recovery methods described in [2] to [11].

Effects of the Invention

A cell recovered by the method of the present invention can provide time-dependent cell information for various types of comprehensive analyses such as genome analysis, transcriptome analysis, proteome analysis, and phosphorylation proteome analysis. As described above, the method according to the present invention can obtain cell information that changes over time, which has been obscured in the conventional methods.

In addition, a conventional gene expression comprehensive analysis (correlational analysis) technique without consideration of detailed temporal before-after relationship, for example, can be developed into a causal analysis technique that clarifies the temporal before-after relationship between gene expressions. That is, using the method according to the present invention makes it possible to expect further revealing of intracellular signaling mechanisms and finding of new drug targets.

The method according to the present invention can recover a cell in a specific state from a cell group and then transport the recovered cell to a different culture environment. This makes it possible to implement a technique of efficiently preparing and recovering cells with high utility values, such as an efficient differentiation induction method for iPS cells. In general, not all stem cells such as iPS cells are differentiated to target cells. Stem cells that are not differentiated have a tumorigenic risk, and hence future regenerative medicine requires to recover only cells with high utility values which are reliably differentiated. In addition, for example, Kato R. et al., have proposed a technique of controlling the quality of pluripotent stem cells by parameter analysis on the morphological features of pluripotent stem cell colonies (Kato R. et al., "Parametric analysis of colony morphology of non-labeled live human pluripotent stem cells for cell quality control." Scientific reports (2016) 6:34009; DOI: 10.1038/srep34009). Using the technique according to the present invention makes it possible to grasp the time-dependent state changes of cells optimal for differentiation induction and cells maintaining pluripotent states. Recovering cells using such state changes as indicators allows this technique to be applied to the quality control of stem cells.

BRIEF DESCRIPTION OF THE DRAWINGS

In FIG. 19, "○" indicates the time point when the signals exceeded the threshold.

BEST MODES FOR CARRYING OUT THE EMBODIMENTS

Figure 1:
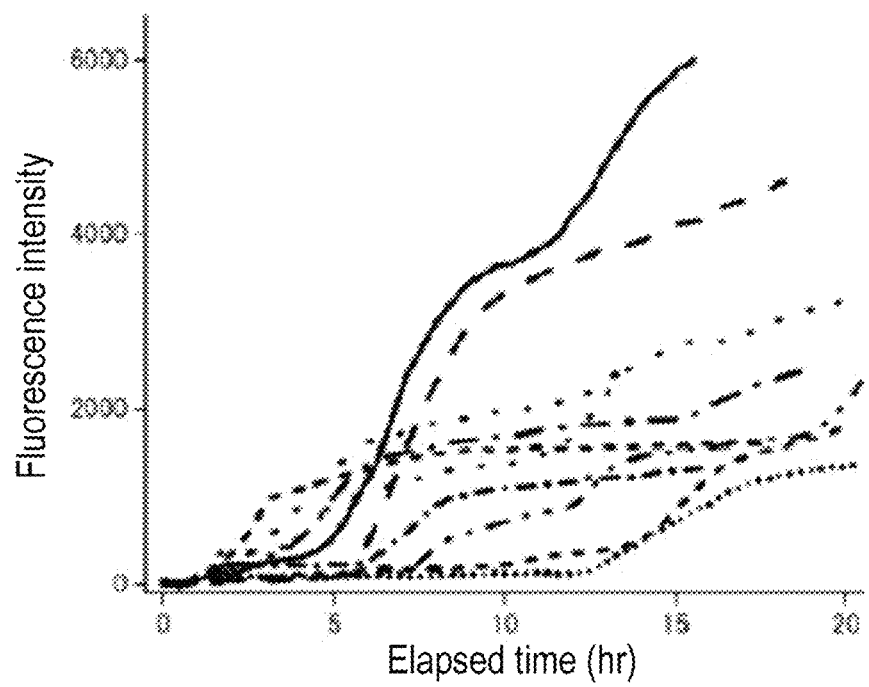
FIG. 1 shows graphs showing the results obtained by chronologically measuring IL-13 secretion amounts from mouse group 2 innate lymphoid cells by using a fluorescence-labeled antibody upon application of IL-33 stimulus (the upper graph in FIG. 1) and IL-2/IL-25 stimulus (the lower graph in FIG. 1). A threshold was obtained by adding a value three times a standard deviation to an average fluorescence intensity in wells containing no cell. The time when the threshold was exceeded is set as the start time point of secretion (elapsed time: 0).
Figure 1:
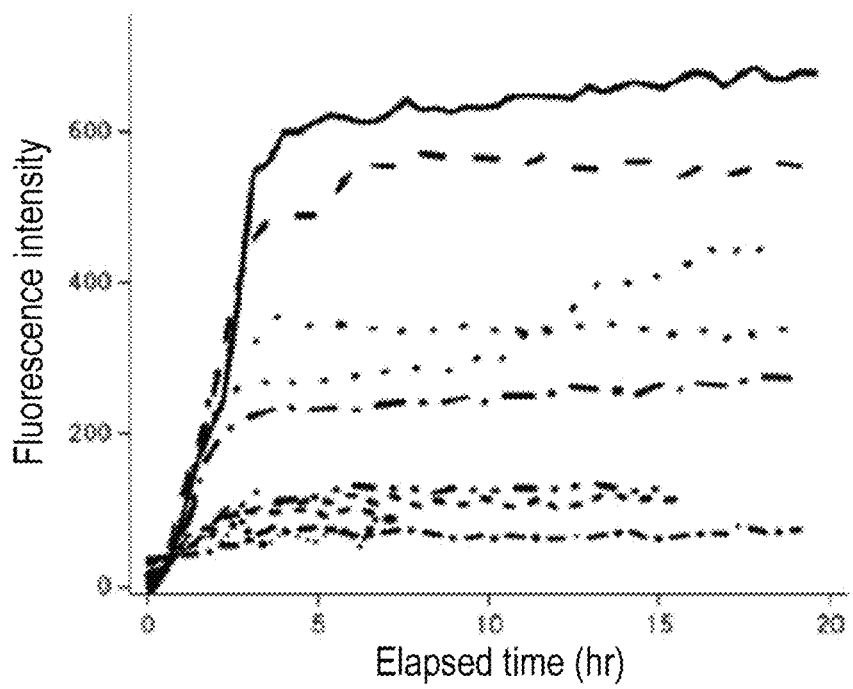

The present invention relates to a method for recovering specific cells from a cell group including a plurality of cells having cell information that changes over time. Note that this method according to one aspect includes:

(a) a step of detecting or measuring a desired indicator in each cell of the above cell group along the time axis; and (b) a step of recovering each cell having undergone a predetermined change in the indicator, wherein the cell is recovered at the time point after the elapse of a preset time since the time point of the predetermined change in the indicator.

In this specification, "cell information" is information indicating the function, feature, and state of a cell, and includes, although not limited to, for example, genetic DNA-sequence information (genome), epigenetic information (DNA methylation, histone methylation, acetylation, or phosphorylation) that controls the expression of genes, gene primary transcript (for example, mRNA, untranslated RNA, or microRNA) information (transcriptome), protein information concerning the translated amounts and the modification such as phosphorylation, oxidation and glycosylation (proteome), metabolite information (metabolome), intracellular hydrogen ion concentration indicator (pH), intracellular ATP concentration, ion concentration (calcium, magnesium, potassium, sodium, or the like), and intracellular temperature.

In this case, cell information that changes over time is cell information that changes with the elapse of time. Note that in a preferred embodiment of the present invention, cell information indicates, for example, cell information that changes in seconds or minutes. Cell information that changes in seconds or minutes includes, for example, gene primary transcript (for example, mRNA) information (transcriptome), protein information concerning the translated amounts and the modification such as phosphorylation, oxidation and glycosylation (proteome), and metabolite information (metabolome).

A method according to the present invention is designed to recover cells while discriminating pieces of cell information that change in such units of time and also recover cells without impairing time resolution with respect to cell information that changes over time.

In this specification, "specific cell" is a cell having specific cell information, which is in the state at the time point after the elapse of a preset time ($\Delta t$) s since the time point of a change in the desired indicator was detected in the target cell. The method according to the present invention is designed to recover a cell having such specific cell information.

Note that a target cell in the method according to the present invention is not specifically limited as long as it is a live cell having cell information that changes over time and allows detection/measurement of a change in the indicator by setting a desired indicator. Such cells include, although not limited to, for example, an immune cell, a nerve cell, a stem cell including an iPS cell and an ES cell, a cancer cell, an endocrine cell, and an exocrine cell. In addition, the origins of cells are not limited to animals including humans and can be any cells such as plant-derived cells and bacteria such as a fungus and a *Bacillus coli*, which are live cells having cell information that changes over time and allow detection/measurement of a change in the indicator by setting a desired indicator.

In this specification, "cell" may be either one cell or a cell group, cell cluster, or cell colony, with two or more cells adhering to each other, as long as an indicator can be detected/measured or recovered as one unit. Accordingly, when a cell group, cell cluster, or cell colony with two or more cells adhering to each other is handled as one unit, "one cell unit" in this specification means a cell group, cell cluster, cell colony, or the like. Note that in the preferred embodiment, "cell" means one cell. That is, in the preferred embodiment, a desired indicator is detected or measured for each cell, and specific cells are recovered one by one from a cell group. However, as described above, an indicator may be detected/measured or recovered for each cell group, cell cluster, or cell colony, with two or more cells adhering to each other, as one unit.

In this case, "indicator" used in the present invention is not specifically limited as long as it can visualize the state change of a desired cell without impairing the cell information of the cell. For example, it is possible to use cell information such as the morphology of a cell (the size or structure of the cell), cell activation, protein expression, or mRNA transcription. Although not limited to the following, a qualitative or quantitative change in the morphology of a cell, cell activation, protein expression, or mRNA transcription can be regarded as "predetermined change in indicator." As a method for detecting or measuring these indicators, it is possible to adopt a known method for each indicator to be used, such as a method using forward scattered light (FSC) or side scattered light (SSC), a method using a fluorescent dye having binding specificity, a method using an artificially fluorescence-labeled protein or nucleic acid, a detection method based on an antibody, and a method using a cell activation indicator. Note that "indicator" is preferably a substance secreted from a cell (for example, a cytokine, interleukin, interferon, protein such as TNF, neurotransmitter such as adrenaline, or hormone).

Note that when a substance (for example, a protein) secreted outside a cell is to be used as an indicator, the protein can be detected or measured by a sandwich immunoassay using an antibody with respect to the protein secreted outside the cell. As described above, when a substance secreted outside a cell is to be used as an indicator, it is preferable in terms of being able to measure a change in indicator by a technique noninvasive to cells to be recovered.

In the method according to the present invention, "indicator" and "predetermined change in indicator" can be properly set for each function or feature of a cell to be recovered or checked. For example, with regard to a cell that secretes a cytokine, the cytokine can be set as "indicator," and the secretion of the cytokine from the cell can be set as "predetermined change in indicator." In this case, "time point of a change in indicator" means the time point when the cytokine was secreted. Note that an external stimulus may be applied to a cell to cause a change in indicator.

A combination of two or more "indicators" can be used, and "predetermined change in indicator" can be properly set in accordance with the "indicators" to be adopted and the number of them. "Time point of a predetermined change in indicator" can be properly set in consideration of "indicator" to be adopted and "predetermined change in indicator" set for each indicator. Although not limited to the following, when, for example, A and B are used as "indicator," the time point when a predetermined change was observed in both A and B can be set as "time point of a predetermined change in indicator."

The method according to the present invention is designed to recover a cell in a state at the time point after the elapse of a preset time since the time point of a predetermined change in "indicator" described above.

In this case, "preset time" is the time ($\Delta t$) set in advance, with the time point of a change in indicator being regarded as the start time point ($t=0$) of measurement. A target cell is recovered at the time point after the elapse of the preset time since the time point of a change in indicator. Such "preset time" can be properly set for each specific cell information of a cell to be finally recovered. Note that a time resolution that can be set as "preset time" is equal to or more than a time resolution in detection or measurement of "indicator." In one embodiment, a time resolution preferably set as "desired time" is a time resolution equal to a time resolution in detection or measurement of "indicator" along the time axis. Note that "preset time" can be properly set to, for example, 30 seconds, 60 seconds, 90 seconds, 5 minutes, 10 minutes, 30 minutes, or 60 minutes after the time point of a change in indicator.

As described above, the method according to the present invention includes (a) "a step of detecting or measuring a desired indicator in each cell of the above cell group along the time axis."

In this case, for a target cell group in the method according to the present invention, a desired indicator is measured in a well containing a culture solution. A well to be used in the method according to the present invention is not specifically limited and a preferable well can be used for each target cell as long as it allows detection or measurement of a change in "indicator" of each cell and enables recovery of each cell to be recovered. Note that a well in which cells are arranged may be one well containing a plurality of cells (cell group) or a well in which each cell of a cell group is placed in separate wells on a cell-by-cell basis.

Note that in one preferred embodiment, the method according to the present invention is performed on an array chip including a plurality of wells each including one cell. Such an array chip is not specifically limited and a commercially available array chip can be used as long as it can contain one cell in each well to be measured. Containing cells one by one (depending on conditions, for example, about 2 to 10 cells) in wells on an array chip is a known method. This method can be executed by preparing a culture solution containing a proper number of cells, introducing the culture solution on an array chip, and performing centrifugal sedimentation.

A suitable culture solution can be used in accordance with a cell to be used or an indicator to be measured. In addition, it is preferable to place a well containing a cell group in an incubator to adjust culture conditions concerning temperature and $CO_2$.

Note that since an indicator can be properly set as described above, it is possible to use, as a measurement technique, a known technique (optical technique or electrical technique) that can measure the indicator and an apparatus to be used in the technique. When an indicator is measured by the optical technique, an optical detection system that can chronologically measure a live cell may be used, and a known optical microscope can be used.

In step (a), a desired indicator is detected or measured along the time axis to specify the time point of a change in indicator. Although it is preferable to continuously detect or measure an indicator along the time axis, detection or measurement can be repeated at predetermined time intervals (for example, every 5 minutes) as long as the time point of a change in indicator can be specified.

One embodiment of the present invention further includes, after the above step (a) and before a step (b) described below, the following step (step (i) of comparing the detected value or the measured value obtained in the above step (a) with a preset threshold and determining a cell having a value exceeding the threshold as a cell that has undergone a predetermined change in indicator and a cell to be recovered from the cell group).

As described above, in one embodiment of the method according to the present invention, in order to specify a cell that has undergone a predetermined change in indicator, a threshold may be set in advance. That is, whether a predetermined change has occurred in an indicator is determined by comparing the detected or measured value obtained in step (a) with a preset threshold. A threshold may be properly set in accordance with a target cell or an indicator to be adopted. In addition, step (i) is designed to spatially recognize a cell having exceeded the threshold as a cell to be recovered from a cell group.

As such a means for comparing a detected value or a measured value with a threshold and/or such a means for spatially recognizing a cell having exceeded the threshold and holding spatial/positional information, programs properly designed by a person skilled in the art or known programs can be used.

One embodiment of the present invention further includes, after the above state (a) and before step (b) described below, the following step (step (ii) of comparing the detected value or the measured value obtained in the above step (a) and its time axis information with a preset threshold to specify the time point when the threshold is exceeded, that is, a step of determining the specified time point as the time point of a predetermined change in the indicator).

As described above, one embodiment of the method according to the present invention, in order to specify the time point of a predetermined change in indicator, a detected value or a measured value, its time axis information, and a preset threshold can be used. In some cases, the time point when an indicator has exceeded a threshold cannot be accurately grasped depending on the time resolution of detection or measurement along the time axis. Even in such a case, the time point of a predetermined change in indicator can be properly determined. For example, it is possible to set the time point of a predetermined change in indicator, a detection or measurement time point immediately before the indicator has exceeded the threshold, or to obtain such a time point by, for example, calculating an approximate curve from consecutive detected values or measured values.

As such a means for comparing a detected value or a measured value and its time axis information with a predetermined threshold and/or a means for specifying the time point when the threshold was exceeded and determining the time point as the time point of a predetermined change in indicator, programs properly designed by a person skilled in the art or known programs can be used.

The method according to the present invention includes (b) "a step of recovering each cell that has undergone a predetermined change in the indicator, and recovering each cell at the time point after the elapse of a preset time since the time point of the predetermined change in the indicator."

After a desired indicator in each cell is detected or measured in step (a), a cell determined as having undergone a change in the indicator is recovered after the elapse of a preset time since the time point of the change in the indicator. Note that as a means for determining the time point after the elapse of a preset time since the time point of a change in indicator, a program properly designed by a person skilled in the art or a known program can be used.

A cell recovery technique is not specifically limited as long as it can recover cells to be recovered for each cell. Cell recovery can be performed by using a system including a glass capillary, a microinjector on which the glass capillary is mounted, and an electrical manipulator (for example, an automatic manipulator or the single cell picking system disclosed in Japanese Patent Application Publication No. 2010-29178) or the like. Note that an automatic apparatus that can automatically recover a cell in accordance with instructions from a program is preferably used in terms of being able to accurately recover a cell with a higher time resolution.

Note that in one embodiment, cells are recovered on a cell-by-cell basis in step (b). That is, in one embodiment of the method according to the present invention, it is possible to recover cells having specific cell information on a cell-by-cell basis from a cell group as a population. According to such an embodiment, it is possible to recover cells having specific cell information on a cell-by-cell basis (preferably, for each cell) even if only a small number of cells constituting a population can be obtained.

In this case, repeating steps (a) and (b) a plurality of times can recover a plurality of cells in a specific state. Such an embodiment can provide a sample constituted by a plurality of cells having specific cell information in an analysis requiring higher sensitivity than single-cell analysis, for example, proteome analysis, and hence is preferable in terms of being able to analyze cell information that cannot be recovered by the conventional recovery methods.

In this case, when the method according to the present invention is an embodiment including step (i) and/or step (ii) in addition to steps (a) and (b), step (i) and/or step (ii) each are repeated a plurality of times. That is, "repeating steps (a) and (b) a plurality of times" includes an embodiment designed to repeat a combination of steps (a), (i), and (b), a combination of steps (a), (ii), and (b), and a combination of steps (a), (i), (ii), and (b).

One embodiment of the method according to the present invention further includes, after step (b), step (c) (a step of correcting the time point of a predetermined change in indicator based on the chronologically obtained information of the indicator and calculating the elapsed time from the corrected time point of the predetermined change in the indicator to the time point of recovery of a cell."

"Correcting the time point of a predetermined change in indicator based on the chronologically obtained information of the indicator" is to recalculate the time point of the predetermined change in the indicator from the chronologically measured data of the indicator with respect to each recovered cell. This makes it possible to recalculate the elapsed time from the corrected time point of the predetermined change in the indicator to the time point of recovery of the cell. The time point of the predetermined change in the indicator can be calculated from the chronologically measured data of the indicator by a method for performing linear regression analysis with respect to measured data.

According to step (c), "time point of a predetermined change in indicator" can be more accurately grasped, and the elapsed time to the time point of recovery can be accurately grasped. Accordingly, for example, when the information of a recovered cell is analyzed, more accurate time axis information can be provided.

In the method according to the present invention, when real-time recovery is performed, in order to calculate the time point after the elapse of a preset time since the time point of the predetermined change in indicator, it is necessary to measure and analyze the indicator. In this case, it sometimes takes much time for analysis processing depending on a selected indicator and the accuracy and performance of analysis programs for real-time recovery, resulting in a decrease in preset time resolution for the recovery of cells. For example, in such a case, step (c) described above allows recalculation of the elapsed time to the accurate time point of a predetermined change in indicator after the recovery of a cell or the time point of recovery of a cell.

In one embodiment of the method according to the present invention, two or more different times can be set as preset times. This makes it possible to recover two or more groups of specific cells in different states. When, for example, a cytokine-secreting cell is to be recovered, setting 30 minutes, 60 minutes, and 90 minutes as predetermined times can recover cells belonging to three groups after the elapse of 30 minutes, 60 minutes, and 90 minutes since the start time point of secretion of a cytokine. According to an aspect of such a recovery method, it is possible to provide time axis information for gene expression analysis and analyze a cause-and-effect relationship concerning each gene expression.

It is preferable to quickly fix a cell after recovery by the method according to the present invention in a fixative solution or by cryopreservation. A preferred fixative solution or cryopreservation conditions to be used may be properly selected for each exhaustive analysis concerning cell information after fixation.

In this case, when a cell after recovery is to be processed by an analysis technique using enzymic activation, cells in a culture solution are preferably recovered into purified water or inorganic saline solution. Purified water or inorganic saline solution used for sample preparation for an analysis technique such as next-generation sequencing preferably contains no RNA degradative enzyme or an inactivated RNA degradative enzyme. In addition, although not limited to the following, inorganic saline solutions that can be used include, for example, phosphate buffered saline (PBS), Hank's balanced salt solution, Earle's balanced salt solution, Gey's balanced solution, and Puck's balanced salt solution. In addition, the lower the salt concentration in the inorganic saline solution used is the better for, for example, next-generation sequencing. For example, it is reported by Ying Zhu et al., that PBS reduces the amplification efficiency concentration-dependently in the RT-PCR method (Ying Zhu et al., "Printing 2-Dimensional Droplet Array for Single-Cell Reverse Transcription Quantitative PCR Assay with a Microfluidic Robot" Scientific reports (2015) 5:9551; DOI: doi:10.1038/srep09551).

When a cell after recovery is recovered into purified water or inorganic saline solution, it is preferable to bring a culture solution in an amount small enough to avoid influence on subsequent analysis into purified water or inorganic saline solution together with the cell without washing or replacing extracellular fluid. Immediately after the cell is recovered into the purified water or inorganic saline solution, fixation processing is preferably performed. The smaller the amount of a culture solution to be brought into the purified water or inorganic saline solution at the time of recovery of the cell, the better. The ratio of a culture solution to the whole inorganic saline solution is preferably 20% or less (v/v). Recovering a cell together with a culture solution can obtain more accurate gene expression analysis information. In contrast to this, if the ratio of a culture solution brought into the whole inorganic saline solution exceeds 20% (v/v), the dissolution of the cell is partially impaired and the nucleus is left in a cell dissolution process.

In one embodiment, at the time point after the elapse of a predetermined time since the time point of a change in indicator, a fixative solution may be directly injected into a well on which a cell to be recovered is present. Directly injecting a fixative solution into the well can fix cell information together with more accurate time information.

A cell after recovery may be quickly transported to a different culture environment. Using the method according to the present invention can contribute to an improvement in differentiation efficiency in a cell differentiation method. For example, using the method according to the present invention makes it possible to recover only a differentiated cell that exists in a preferred state (for example, a cell in a state optimal fora shift to the subsequent culture conditions) after the elapse of a predetermined time since a change in indicator from a sell group containing cells in undifferentiated and differentiated states. In addition, for example, it is possible to recover a cell that produces a specific substance with high productivity from a cell group. A cell recovered in this manner can also be transported to a medium or the like in preferred culture conditions, as needed.

Note that a preferred embodiment of the method according to the present invention relates to a method for measuring a protein secreted as an indicator from a cell by using a single cell secretion imaging technique.

The single cell secretion imaging technique is a sandwich immunoassay method using evanescent light originating from total internal reflection fluorescence illumination. Note that as an array chip used in the single cell secretion imaging technique, for example, the array chip prepared by the method disclosed in literature information such as Sci Rep. 4:4736, 2014 (Non-Patent Literature 3) can be used. This array chip is prepared by overlaying an optical microscope grade cover glass and a resin on each other. For example, it is possible to use an array chip having a well structure formed by a photosensitive resin that is low in cytotoxicity and allows gm size fabrication, such as polydimethylsiloxane, SU-8® available from Nippon Kayaku, or TMMR NR-0034® available from Tokyo Ohka Kogyo Co., Ltd. Evanescent light by total internal reflection fluorescence illumination can be homogeneously formed by using a resin having a refractive indicator equal to that of water (1.334) such as CYTOP® available from Asahi Glass Co. as an connection layer between the resin and the glass forming the well structure of the array chip. The resin and the glass are preferably joined to each other with strength high enough to prevent them from peeling off when they are immersed in acetone, alcohol, aqueous solution, or the like. Such joining can be implemented by an aminosilane surface treatment and air plasma surface modification.

For total internal reflection fluorescence illumination, a known total internal reflection fluorescence microscope can be used.

Using such an array chip makes it possible to locally perform fluorescence excitation at about 100 nm near each bottom surface of concave well in the array chip by using total internal reflection fluorescence illumination. With this operation, for example, using a sandwich immunoassay using an antibody with respect to an indicator bonded to a well bottom surface and a fluorescence detection antibody makes it possible to specifically measure the indicator bonded to the antibody on the well bottom surface.

The single cell secretion imaging technique can detect or measure, as an indicator, any substance that is secreted from a cell and can be detected by sandwich immunoassay.

Note that as another aspect, the present invention provides a system for executing the method according to the present invention described above. According to one preferred embodiment, this system is constituted by (1) a well, (2) a detection unit, (3) an analyzing unit, and (4) a recovering unit.

(1) Well

The well to be used is not specifically limited to any size, shape, and the like and a suitable well can be used as needed as long as it allows detection or measurement of a change in "indicator" of each cell and recovery of each cell to be recovered.

Target cells are arranged in wells, and "indicator" is detected or measured by the detection unit for each cell.

(2) Detection Unit

A suitable detection device can be used as needed for each "indicator." For example, when "indicator" is optically detected or measured along the time axis, images can be chronologically obtained by using a fluorescence microscope. When the single cell secretion imaging technique is used, images can be chronologically obtained by using a total internal reflection fluorescence microscope. In addition, the image data obtained by the detection unit is sent to the analyzing unit.

Note that when an array chip on which 100 to 1,000 cells can be arranged is used, all the cells on the array chip may not be simultaneously imaged. In such a case, one array chip can be divided into a plurality of segments, and cells can be sequentially imaged for each segment. Accordingly, a predetermined time interval occurs between the first imaging operation and the second imaging operation with respect to a specific cell, and the cell is consecutively imaged at predetermined time intervals.

(3) Analyzing Unit

The analyzing unit analyzes the image detected by the detection unit. The analyzing unit includes i) a means for calculating a detected value or measured value from the image obtained by the detection unit and determining a cell to be recovered from the calculated detected value or calculated measured value, ii) a means for determining the time point of a predetermined change in indicator from the detected value or measured value and time axis information, and/or iii) a means for determining the time point after the elapse of a preset time since the time point of a predetermined change in indicator.

Note that i) the means for determining a cell to be recovered from a calculated detected value or calculated measured value can compare the detected value or measured value with a preset threshold to determine, as a cell to be recovered, a cell exceeding the threshold in one embodiment. In addition, the analyzing unit acquires and holds spatial/positional information of a cell from an obtained image. The spatial/positional information is transmitted to the recovering unit to specify the position of the cell determined to be recovered. In addition, ii) the means for determining the time point of a predetermined change in indicator from the detected value or measured value and time axis information can compare the detected value or measured value and its time axis information with a preset threshold to specify the time point when the threshold is exceeded and to determine the time of a predetermined change in indicator in one embodiment.

(4) Recovering Unit

The recovering unit operates in cooperation with the analyzing unit. A manipulator or the like automatically suctions a cell specified by the analyzing unit as a cell that has undergone a predetermined change in indicator and is located at the time point after the elapse of a preset time since the time point of the predetermined change in indicator. The cell is then discharged/recovered into a well containing a fixative solution or another culture solution, etc.

In one embodiment, the system according to the present invention can also include (5) a control unit that comprehensively controls two or more (preferably, all) of (1) the well, (2) the detection unit, (3) the analyzing unit, and (4) the recovering unit.

According to another aspect, the present invention provides a method for analyzing a cell recovered by the method according to the present invention. The cell information of a cell recovered by the present invention can be a target for analyses from various viewpoints, such as genome analysis, transcriptome analysis, proteome analysis, and phosphorylation analysis. Accordingly, an analysis method for a cell recovered by the method according to the present invention is not specifically limited as long as it is designed to analyze cell information. Note that the method according to the present invention provides cell information added with time axis information, which has been obscured by the conventional methods, and is expected to obtain new findings from the cell information.

Note that the terms used in this specification are used to describe specific aspects, and are not used to limit the present invention.

The term "include" or "comprise" in this specification intends to indicate that the described particulars (steps, elements, and the like) are present, and do not exclude that other particulars (steps, elements, and the like) are also present, unless it should obviously be interpreted differently from the description of the specification.

Unless otherwise defined, the terms used in this specification have the same meanings as those generally appreciated by a person skilled in the art. The terms used in this case should be interpreted to have meanings consistent with the contextual meanings in the specification and the related technical fields, and should not be interpreted to have ideal or excessively formal meanings, unless otherwise defined clearly.

The references in this specification are incorporated herein by reference in the specification.

The present invention will be described in more detail below with reference to Examples. However, it should not be interpreted to be limited to Examples described below.

EXAMPLES

A specific Example of the present invention will exemplify a method for recovering live cells on a cell-by-cell basis when a preset time $\Delta t$ has elapsed since the time point of a change in an indicator of the state of each live cell and a technique of analyzing cell information held by each recovered cell.

In this Example, "cell secretion" was employed as an indicator of a change in the state of a live cell, and "single-cell secretion measurement" was used as an indicator measurement method. Cell secretion is cell information which a cell outputs circumferentially in response to external stimulus or spontaneous intracellular state change. In classical cell secretion via vesicular transport, the secretion volume is generally thought to be proportional to the transcript amount of messenger RNA (mRNA) as a synthetic template of the secreted protein. However, details cannot be revealed from multicellular analysis (Cancer Epidemiol Biomarkers Prev. 19(4):978-81 (2010)).

In this Example, IL-13 secretion response to IL-33 stimulus or IL-2/IL-25 stimulus to mouse group 2 innate lymphoid cells (Nature. 463, 540-4, 2010) was measured, and cells were recovered on a cell-by-cell basis after the elapse of Δt since the start time point of secretion response. The cells were then frozen and fixed, and expression level analysis of intracellular I113 mRNA (the upper case letters "IL" represent an interleukin mRNA) was performed.

Example 1

Measurement of Cell Secretion on Minute-by-Minute Basis with Reference to Cell State Change as Indicator First, each cell secretion was observed on a minute-by-minute basis based on the single-cell secretion real-time imaging technique disclosed in Sci Rep. 4:4736, 2014 (Non-Patent Literature 3). This operation will be described in detail below.

Mouse group 2 innate lymphoid cells used in this Example were obtained as follows. Mouse group 2 innate lymphoid cells were harvested from mouse intestinal membrane fat-associated lymphoid cluster (FALC) and purified. The purified lymphoid cells were then cultured for a long period of time in a culture solution (RPMI1640 medium, 1×MEM NON-ESSENTIAL AMINO ACID SOLUTION, 10 mM HEPES, 1 mM Sodium Pyruvate, 100 U/ml Penicillin, 100 µg/ml Streptmycin, 55 µM 2-Mercaptoethanol, 50 ng/ml gentamicin sulfate, and 10% FCS) in an incubator at 37° C. with 5% $CO_2$, in the presence of IL-2 (final concentration of 10 ng/mL, Recombinant Mouse IL-2 protein, 402-ML available from R&D Systems). A concave well array chip used in the measurement was prepared by joining a 45-µm thick polydimethylsiloxane resin having an array of 40 µm diameter through holes (SYLGARD® 184 SILICONE ELASTOMER KIT available from Dow Corning) to an optical microscope grade cover glass (round cover glass CO25001 available from Matsunami Glass Ind., Ltd). Anti-mouse IL-13 capture antibody (Cat #MAB413 available from R&D Systems) was solid-phased on the glass bottom surface of each concave well. Mouse group 2 innate lymphoid cells were introduced into the concave well array chip by about 400 to 800 per 1,000 concave wells, and were randomly arranged in concave wells by centrifugal sedimentation at 100 xg for 30 seconds. Cells outside the concave wells were removed by medium replacement. Anti-mouse IL-13 detection antibody (Cat #BAF413 available from R&D Systems and CF660R Streptavidin, Cat #29040 available from Biotium) fluorescence-labeled via avidin-biotin was added at 30 nM to the observation medium. Measurement was performed with an electrical inverted microscope system (ECLIPSE Ti-E available from Nikon Corporation) including total internal reflection fluorescence. Imaging was performed with the high-sensitivity EM-CCD camera (Ima-gEM-1K available from Hamamatsu Photonics K.K.) mounted in the above system. After the concave well array chip was installed, mouse IL-33 (final concentration of 10 ng/mL, Recombinant Mouse IL-33 Protein, Cat #3626-ML available from R&D Systems) or mouse IL-2/IL-25 (final concentration of 10 ng/mL, Recombinant Mouse IL-17E Protein, Cat #1399-IL available from R&D Systems) was added to the cells, and IL-13 secretion volumes were measured. IL-13 secreted from each cell was quickly captured by the antibody on the concave well bottom surface, and subsequently was dyed by the fluorescence detection antibody in the medium. In general sandwich immunoassay, an uncombined fluorescence detection antibody is removed, and the fluorescence amount of the remaining combined detection antibody is measured, thereby quantitatively measuring an antigen. In the single-cell secretion real-time imaging technique in this Example, it is possible to specifically measure the fluorescence amount of detection antibody combined with the antigen in the presence of the uncombined fluorescence detection antibody by locally performing fluorescence excitation at about 100 nm near each concave well bottom surface in total internal reflection fluorescence. By using this technique, IL-13 secretion from each of 162 or 180 cells was intermittently measured at time intervals of 27 minutes for 1,200 minutes. FIG. 1 shows changes in the increments of fluorescence from top 10 cells in terms of secretion volume in the presence of IL-33 and IL-2/IL-25 stimuli, that is, the cumulative amount of secreted IL-13, with the elapse of time from the start time point of secretion. At the start time point of secretion, discrimination was performed by using, as a threshold, a value obtained by adding a value three times a standard deviation to an average fluorescence intensity in concave wells containing no cell.

As shown in FIG. 1, signals from mouse group 2 innate lymphoid cells stimulated by IL-33 kept increasing, and the lymphoid cells tended to keep secreting IL-13. In contrast to this, signals from mouse group 2 innate lymphoid cells stimulated by IL-2/IL-25 increased for several hours and then stopped changing. That is, the lymphoid cells tended to transiently secrete IL-13 and then stop secreting. It was expected from these results that I113 mRNA in mouse group 2 innate lymphoid cells continuously existed in the presence of IL-33 stimulus, but was transiently transcripted and quickly decomposed in the presence of IL-2/IL-25 stimulus.

Example 2

Figure 2:
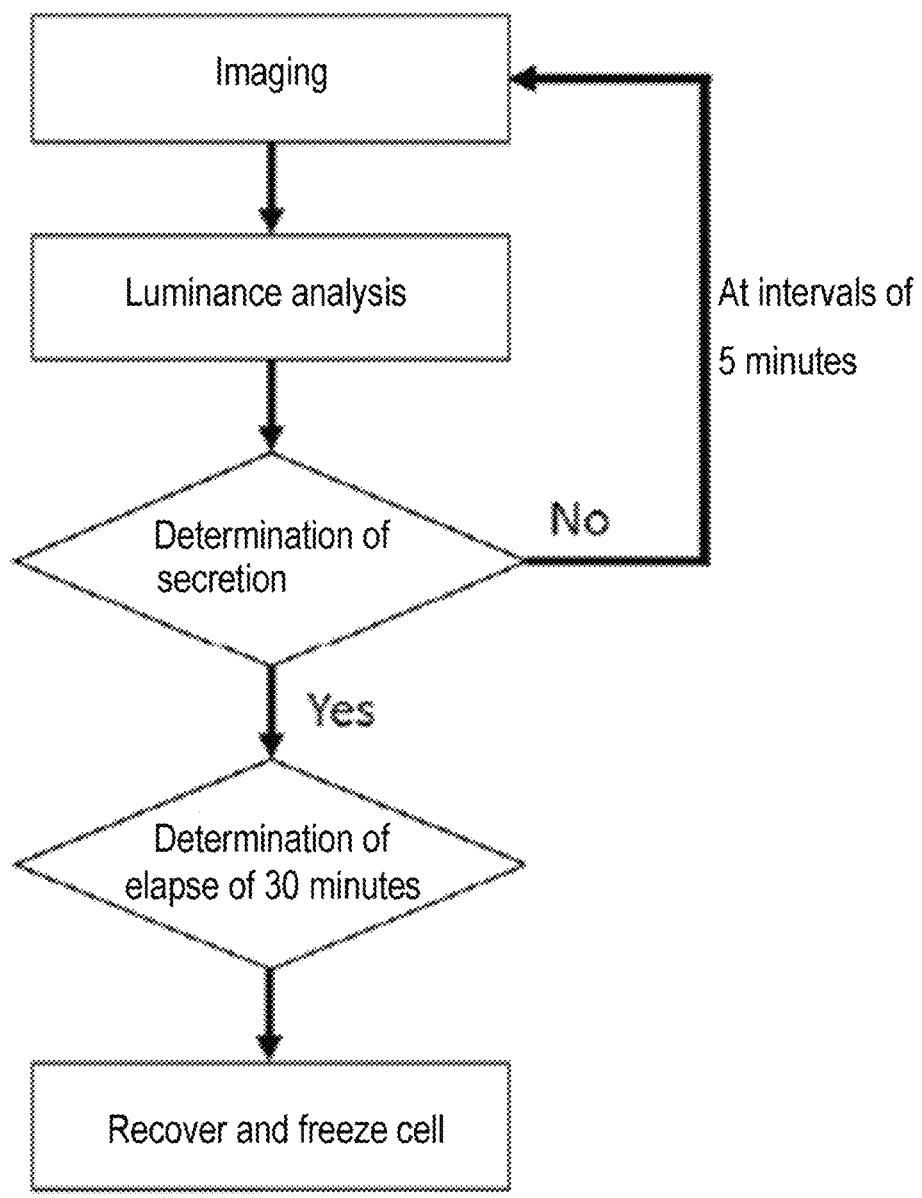
FIG. 2 is a flowchart from cell imaging to recovery/freezing in a test conducted in Example 2 in this specification.

Recovery (Real-Time Cell Recovery) and Fixation of Cell Information at Time Point after Elapse of Preset Time Since Start of Cell Secretion Regarded as Change in Indicator of Cell State The start of IL-13 secretion from mouse group 2 innate lymphoid cells stimulated by IL-33 was used as an indicator of a change in cell state based on the findings in Example 1. Mouse group 2 innate lymphoid cells were recovered in real time after the elapse of 30 minutes since the start of IL-13 secretion (that is, recovery was performed upon setting a predetermined elapsed time since the time point of a change in indicator to 30 minutes), and cell information fixation was executed by a freezing treatment. IL-13 secretion was measured by the same method as that in Example 1 described above. Note, however, that although only imaging was performed in real time in Example 1, fluorescence intensity analysis, secretion determination, and time-lapse determination were executed in real time following imaging based on a microscope control imaging program (NIS-Elements AR available from Nikon Corporation) and a custom-built program (Visual Basic available from Microsoft Co.) as indicated by the flowchart of FIG. 2 in Example 2. In determining the start time point of secretion from a cell, wells containing no cell were designated in advance, and the value obtained by adding a standard deviation to the average fluorescence intensity of the designated wells was used as a threshold. Each cell determined as positive in secretion determination was assigned with the immediately preceding imaging time point (imaging immediately before imaging used for secretion determination) as the start time point of secretion, and the cell was recovered on a cell-by-cell basis at the time point after the elapse of 30 minutes since the start time point of secretion. In this recovery, each cell was manually suctioned, together with a small amount of the medium, under microscope observation, with a pneumatic microinjector (IM-11-2 available from Narishige Group) equipped with a glass capillary having an inner diameter of 15 µm (L-Tip 15 µm 60° 15 mm available from YODAKA GIKEN K.K.) and an electrical manipulator (electrical micromanipulator TransferMan NK2 available from Eppendorf AG), and was discharged into 2.5 µL 2× Reaction Mix (CellsDirect One-Step qRT-PCR Kit available from ThermoFisher Scientific) dispensed in a 0.2 ml PCR tube with a dome cap. After the cell was discharged, the cap was quickly closed, and spinning down was performed by a tabletop microcentrifuge (PMC-060 available from TOMY SEIKO CO., LTD.). Thereafter, the cell was rapidly frozen in liquid nitrogen and preserved at −80° C.

Figure 3:
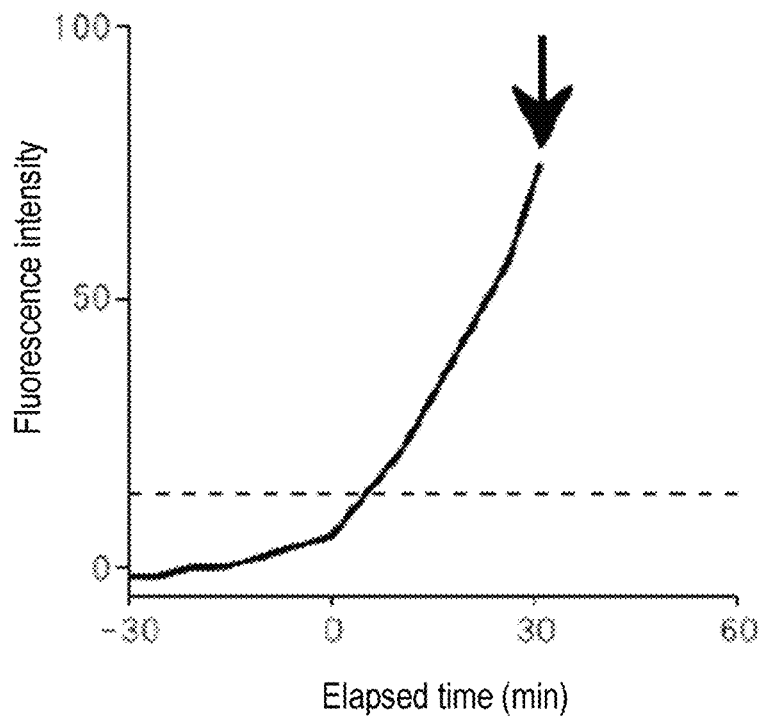
FIG. 3 is a graph showing the result obtained by chronologically measuring, with a fluorescence-labeled antibody, an IL-13 secretion amount from a mouse group 2 innate lymphoid cells (one of five cases), which secreted IL-13 upon application of IL-33 stimulus and was recovered 30 minutes after the start time point of secretion. The abscissa represents the elapsed time from the start time point of secretion (t=0), which is the time point immediately before the fluorescence intensity of a recovered cell exceeded a threshold. The ordinate represents increases in fluorescence intensity due to IL-13 secretion. The broken line indicates the threshold used for the detection. The arrow indicates the time point of recovery. The threshold is the value obtained by adding a standard deviation to an average fluorescence intensity in wells containing no cell.

With the above work, five cells were recovered in real time, with secretion being an indicator. FIG. 3 is a graph showing the measurement result obtained by chronologically measuring a fluorescence intensity with respect to one example of the recovered cells. Referring to FIG. 3, the abscissa represents the elapsed time, with the start time point of secretion being 0, and the ordinate represents increases in fluorescence intensity originating from IL-13 secretion. The broken line indicates the threshold used for the detection. The arrow indicates the time point of recovery.

Before real-time recovery, two cases of cells before application of IL-33 stimulus were recovered on a cell-by-cell basis, and were rapidly frozen in the same manner as described above.

Figure 4:
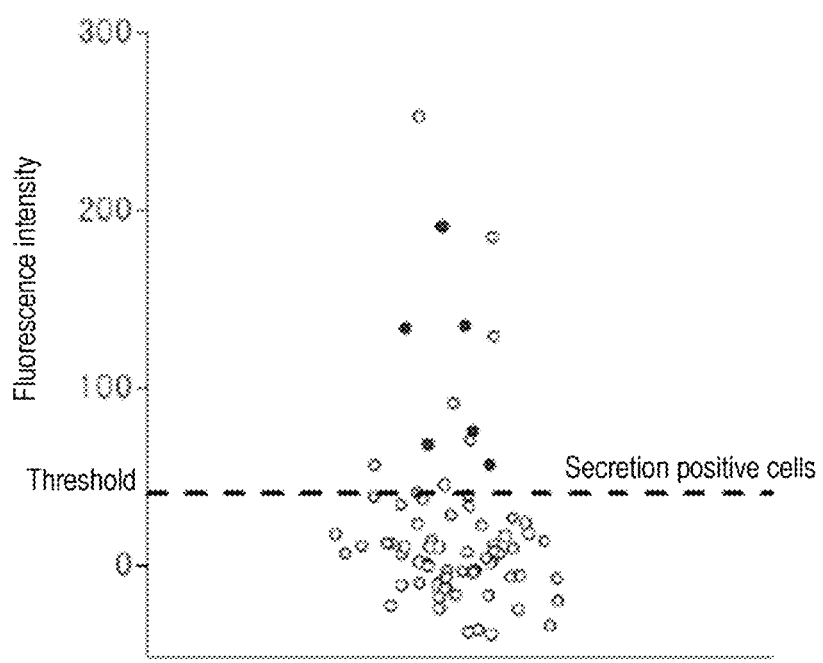
FIG. 4 is a graph showing IL-13 secretion amounts at end points of measurement as "○" in wells each containing one cell, which is a mouse group 2 innate lymphoid cells that secreted IL-13 upon application of IL-33 stimulus. The ordinate in the graph of FIG. 4 represents fluorescence intensities corresponding to the IL-13 secretion amounts. The broken line indicates a threshold. The threshold was obtained by adding a value three times a standard deviation to the average fluorescence intensity in wells containing no cell. Cells that exceeded the threshold were regarded as secretion-positive mouse group 2 innate lymphoid cells some of which were collectively recovered (six cases). The recovered secretion-positive mouse group 2 innate lymphoid cells were indicated by "●."

Following the real-time recovery, in comparison with the above operation, secretion positive cells at the end time of measurement, which had no time-dependent information concerning a change in indicator, were recovered (collective recovery at end point of measurement) in the same manner as described above. The end point of measurement was set to the time point after the elapse of 8 hours since application of stimulus. More specifically, six cases of secretion positive cells at the end point of measurement (FIG. 4) were recovered on a cell-by-cell basis and were rapidly frozen in the same manner as described above. When the elapsed times from the start time points of secretion were checked with respect to the secretion positive cells, the elapsed times vary between 60 minutes and 120 minutes.

Example 3

Analysis of Intracellular Information of Mouse Group 2 Innate Lymphoid Cells Recovered in Real Time with IL-13 Secretion being Indicator The Il13 mRNA amounts, i.e., intracellular information, of mouse group 2 innate lymphoid cells recovered in real time and frozen-preserved, with IL-13 secretion being an indicator in Example 2 were measured, together with the Gapdh mRNA amounts, by the target specific multiplex reverse transcription quantitative PCR method (Nat Protoc. 9(7): 1713-26, 2014). The measurement results were compared and calculated by the ΔCt method with reference to Gapdh. Likewise, the Il13 mRNA amounts of the mouse group 2 innate lymphoid cells (together with secretion positive cells and secretion negative cells) collectively recovered at the end point of measurement were measured.

More specifically, after each mouse group 2 innate lymphocyte discharged into 2.5 µL 2× Reaction Mix and frozen was melted, a quantitative PCR assay (PrimeTime® Predesigned qPCR Assay Mix, Assay ID: Mm.PT.39a.1 available from Integrated DNA Technologies, Inc./TaqMan® Gene Expression Assay Mix, Assay ID: Mm00434204 ml available from ThermoFisher Scientific) targeted to SuperScript® III RT/Platinum® Taq Mix 0.1 µL, Gapdh mRNA, and Il13 mRNA was added at a final concentration of 0.05× (each 45 nM primer and 12.5 nM double indicator probe) to prepare DEPC-treated water with a total liquid volume of 5 µL. The reaction solution was reverse-transcripted at 50° C. for 15 minutes. The resultant solution was then pre-amplified under the condition of repeating the step of performing thermal denaturation at 95° C. for 15 seconds and the step of performing synthesis at 60° C. for 4 minutes over 14 cycles. The pre-amplified product was diluted with DEPC-treated water with a total liquid volume of 50 µL. Of the resultant solution, 1 µL of solution as a template was subjected to quantitative PCR by using StepOnePlus Real-Time PCR Systems available from Applied Biosystems in accordance with the manual for TaqMan Fast Universal PCR Master Mix. Quantitative values Ct of each cell and each gene were calculated by software (StepOne software available from Applied Biosystems) attached to an apparatus. The IL13 mRA expression level of each cell was compared with the ΔCt value obtained by subtracting the Ct value of Il13 mRNA from the Ct value of Gapdh mRNA.

Figure 5:
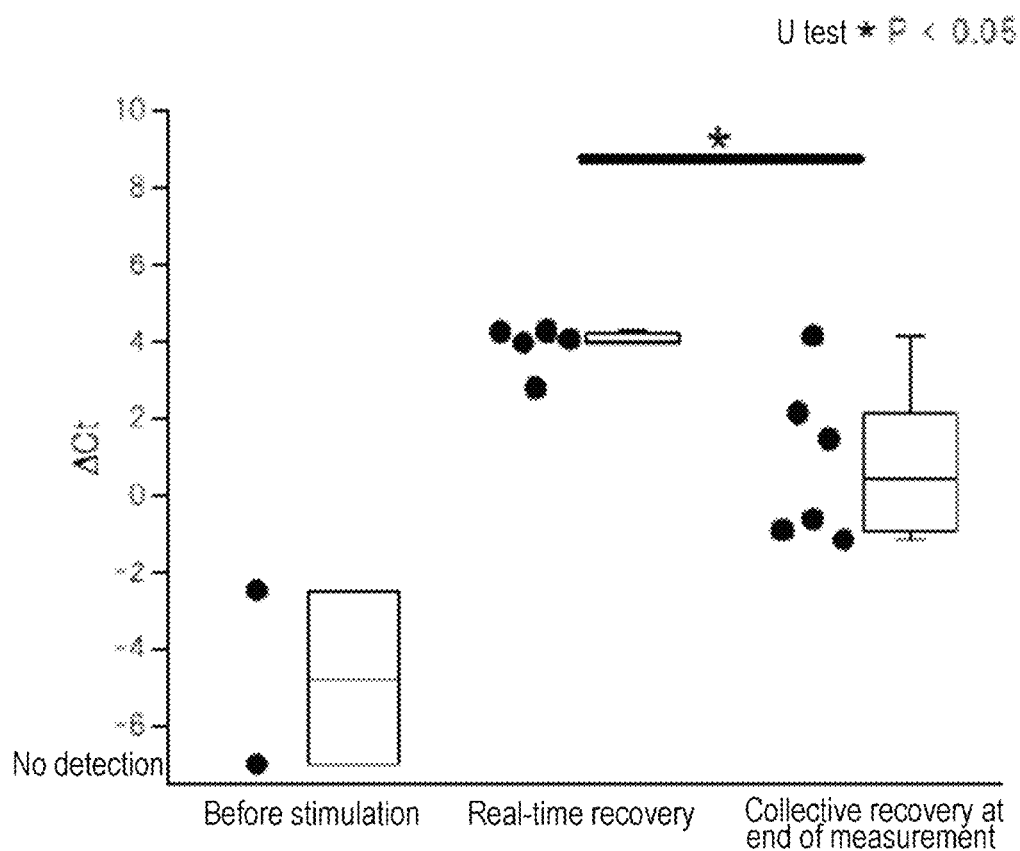
FIG. 5 is a graph showing the results obtained by measuring Il13 mRNA amounts, by a target-specific multiplex reverse transcription quantitative PCR method, in mouse group 2 innate lymphoid cells collectively recovered before application of IL-33 stimulus, mouse group 2 innate lymphoid cells recovered in real time (recovered 30 minutes after the start time points of secretion) with IL-13 secretion as an indicator after application of IL-33 stimulus, and secretion-positive mouse group 2 innate lymphoid cells collectively recovered at end points of measurement. Each ΔCt value was calculated by subtracting the Ct value of Il13 mRNA from the Ct value of Gapdh mRNA. In addition, "★" represents $P<0.05$ (U test).

FIG. 5 shows the results. FIG. 5 shows the ΔCt values of Il13 mRNA in mouse group 2 innate lymphoid cells recovered in real time before application of stimulus, with secretion being an indicator, or collectively recovered at the end point of measurement (secretion positive) in the forms of point sequences and box-and-whisker plots by using OriginPro 2015. Each point of the point sequences corresponds to one cell. The larger the ΔCt value, the more Il13 mRNA is contained in each cell. Significant differences were evaluated by U test. A high Il13 mRNA ΔCt was detected from each of the cells recovered in real time, with secretion being an indicator, thus indicating that a relatively larger amount of Il13 mRNA was expressed than in collectively recovered secretion positive cells. In contrast, no Il13 mRNA or a very small amount of Il13 mRNA was expressed in mouse group 2 innate lymphoid cells before application of stimulus. These experimental results revealed that mouse group 2 innate lymphoid cells that secreted IL-13 upon application of IL-33 stimulus held large amounts of Il13 mRNA immediately after the start of secretion, that is, at the time of vigorous secretion, but the amounts of Il13 mRNA were not maintained and reduced after the elapse of 60 minutes to 120 minutes. It is considered that variations over time in IL-13 secretion volume upon application of IL-33 stimulus shown in FIG. 1 reflect dynamic variations in Il13 mRNA.

Example 4

Differences in Gene Expression Mode Depending on Application of Stimuli

As indicated by Example 1 described above, the mouse group innate lymphoid cells also secrete IL-13 protein upon application of IL-2/IL-25 stimulus. Unlike the mouse group 2 innate lymphoid cells stimulated by IL-33, the mouse group 2 innate lymphoid cells stimulated by IL-2/IL-25 tended to stop secreting upon transiently secreting IL-13 protein. This experiment checked whether the amounts of Il13 mRNA in cells upon application of IL-2/IL-25 stimulus transiently increased and then quickly decreased as in the case of IL-13 secretion.

Figure 6:
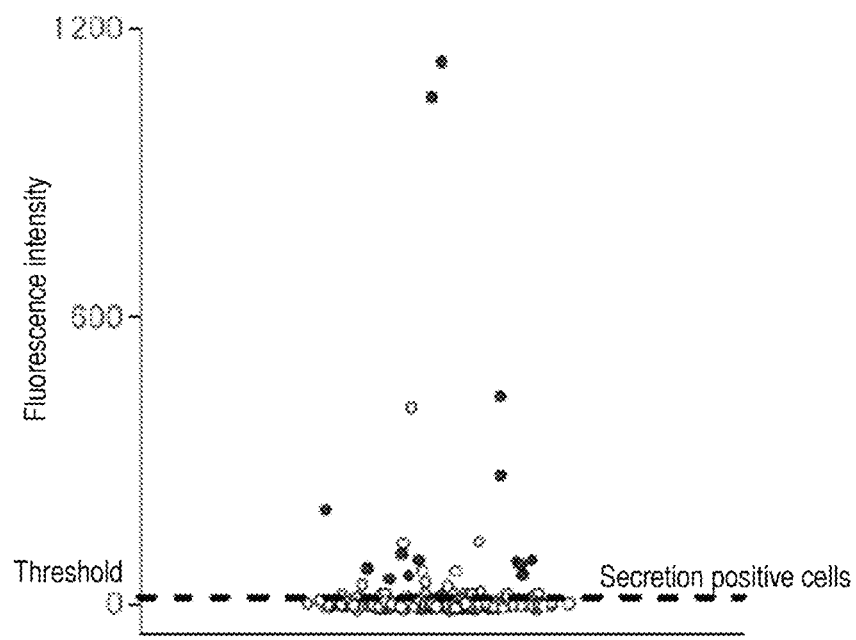
FIG. 6 is a graph showing IL-13 secretion amounts at end points of measurement as "○" in wells each containing one cell, which is a mouse group 2 innate lymphoid cells that secreted IL-13 upon application of IL-2/IL-25 stimulus. The ordinate in the graph of FIG. 6 represents fluorescence intensities corresponding to the IL-13 secretion amounts. The broken line indicates a threshold. The threshold was obtained by adding a value three times a standard deviation to the average fluorescence intensity in wells containing no cell. Cells that exceeded the threshold were regarded as secretion-positive mouse group 2 innate lymphoid cells, some of which were collectively recovered (15 cases). The recovered secretion-positive mouse group 2 innate lymphoid cells were indicated by "●."
Figure 7:
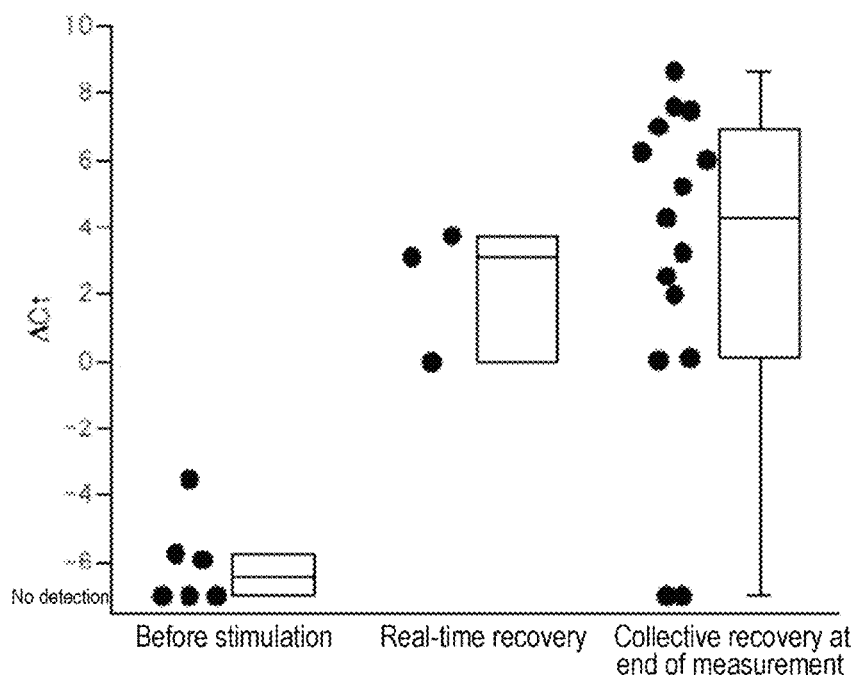
FIG. 7 is a graph showing the results obtained by measuring Il13 mRNA amounts, by a target-specific multiplex reverse transcription quantitative PCR method, in mouse group 2 innate lymphoid cells collectively recovered before application of IL-2/IL-25 stimulus, mouse group 2 innate lymphoid cells recovered in real time (recovered 30 minutes after the start time points of secretion) with IL-13 secretion as an indicator after application of IL-2/IL-25 stimulus, and secretion-positive mouse group 2 innate lymphoid cells collectively recovered at end points of measurement.

As in Example 2, three cells were recovered in real time and frozen at the time point after the elapse of 30 minutes since the start time point of secretion. In comparison, cells at the end point of measurement were recovered. It has been known that IL-2/IL-25 stimulus produces less IL-13 secretion than IL-33 stimulus (Nature. 463, 540-4, 2010). In this experiment as well, the number of IL-13 secretion positive cells was small. For this reason, a time long enough for many cells to respond was provided after the endpoint of measurement, and fluorescence intensities in 2,400 wells were measured 24 hours after application of stimulus (FIG. 6). Then, 15 secretion positive cells were collectively recovered and frozen in the same manner as described above. The ΔCt values of Il13 mRNA in the frozen cells with respect to Gapdh mRNA were measured and calculated by quantitative PCR as in the same manner in Example 3. FIG. 7 shows the results. As shown in FIG. 7, contrary to the initial expectation, the Il13 mRNA amounts of the secretion positive cells at the endpoint of measurement were not reduced as compared with the case of real-time recovery. This result indicated that, in the case of IL-2/IL-25 stimulus, the Il13 mRNA amounts were maintained even after the stoppage of IL-13 secretion.

Figure 8:
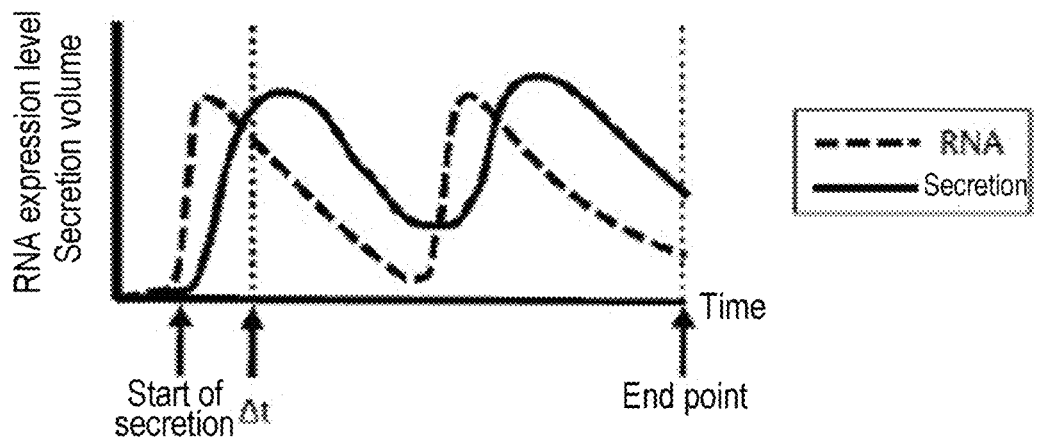
FIG. 8 schematically shows graphs of time-dependent changes (dynamic gene expression) in the Il13 mRNA expression levels and IL-13 secretion amounts of mouse group 2 innate lymphoid cells upon application of IL-33 stimulus and time-dependent changes (static gene expression) in the 1113 mRNA expression levels and IL-13 secretion amounts of mouse group 2 innate lymphoid cells upon application of IL-2/IL-25 stimulus.
Figure 8:
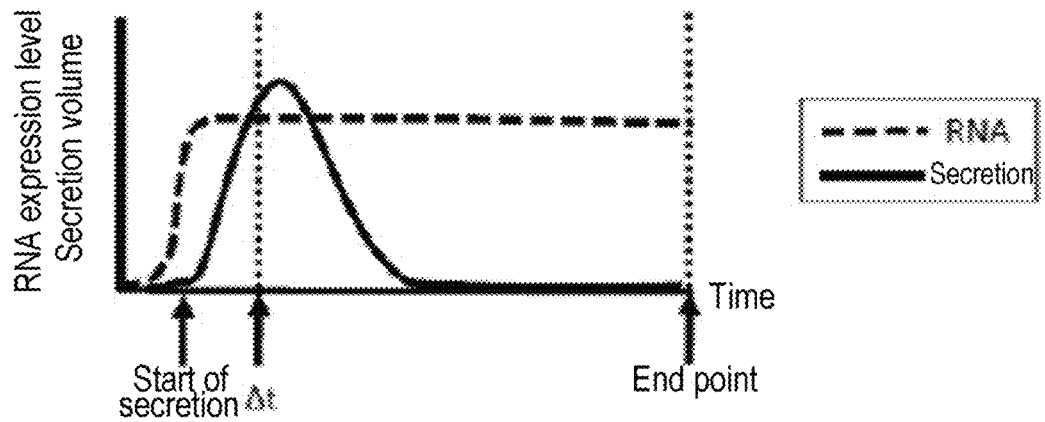

Although mouse group 2 innate lymphoid cells secreted IL-13 in response to IL-33 stimulus, its secretion mode was persistent while changing the secretion volume. The Il13 mRNA amounts of cells recovered in real time at the time after the elapse of 30 minutes since the start of secretion, that is, at the time point of vigorous secretion, were significantly larger than the mRNA amounts of cells collectively recovered at the end point of measurement. This indicates that Il13 mRNA is dynamic gene expression, which varies in amount moment to moment. In contrast to this, although the mouse group 2 innate lymphoid cells transiently secreted IL-13 in response to IL-2/IL-25 stimulus, there were almost no differences between the Il13 mRNA amounts from cells recovered in real time and those from cells recovered collectively at the time point after the elapse of a sufficient period of time since application of stimulus. This indicates that Il13 mRNA is static gene expression, which holds its amount after transcription (FIG. 8). Dynamic gene expression has the property of strongly reflecting the cell state at that moment, and hence can be used as cell information indicating cell activation. Static gene expression has the property of reflecting a change in the state of the cell for a long period of time, and hence can be cell information that can be used for cell classification. Even the same type of gene in the same type of cell can change between dynamic gene expression and static gene expression depending on stimulus. This is an interesting finding that has been demonstrated by this Example for the first time.

This Example has demonstrated that the states of cells recovered in real time can be unified by forcibly synchronizing the different timings of the state changes of the respective cells, with each state change being an indicator, to result in revealing the time-dependent features of gene expression in the cells.

Although this Example has exemplified the manual recovery method, cell recovery can be executed by an apparatus such as a manipulator that can automatically recover cells based on information and determination from an indicator detection/measurement means, a means for determining a change in indicator, a means for determining the elapse of a preset time from a change in indicator, and the like. Increasing work efficiency by, for example, automating recovery makes it possible to improve the real-time recovery work at the time point after the elapse of the time Δt.

This Example has exemplified mRNA expression analysis with respect to two types of genes. It is, however, easily conceivable that time-dependent gene expression analysis can be exhaustively performed by using the existing single-cell target-specific multiplex reverse transcription quantitative PCR method (Nat Protoc. 9(7): 1713-26, 2014) and single-cell RNA-seq (Genome Biol. 14(4):R31, 2013).

Example 5

Example 5 has studied the possible influences of conditions for recovery of one cell from a cell activation measurement environment on analysis results in a case of recovering cells on a cell-by-cell basis at the time point after the elapse of a preset time Δt and exhaustively analyzing the polyA RNA expression level held by the cell.

This Example used a suction recovery method using a glass capillary as a technique of recovering one cell. In a method for recovering a cell external solution together with a cell as in this technique, when a sample after recovery is applied to an analysis technique using enzymatic activation, influences, e.g., inhibition, of the brought solution on enzymatic activation are generally conceivable. For example, in a general preparation method for a next-generation sequencing sample, it has been suggested that the brought amount of a culture supernatant for cells has serious influences on results, and that cells are replaced with an inorganic saline solution such as a phosphate buffered saline (PBS(-)) containing no calcium or magnesium. For this reason, the Example examined the influences of a brought solution in a cDNA amplification step to be performed before polyA RNA from one cell was analyzed by the next-generation sequencing method.

The cells used in this Example were mouse group 2 innate lymphoid cells as in Example 1. As a solution for suspending cells, 0.1× PBS (obtained by mixing PBS (-) with RNase-free water at 1:9 (v/v)) or a mixture of these solutions was prepared, and 1 µL of 10× Lysis Buffer contained in a reagent kit (SMART-Seq®) v4 3' DE Kit (635040 available from Clontech) designed for synthesis and amplification of cDNA from poly A RNA was added to each solution (10 µL) in which mouse group 2 innate lymphoid cells were suspended. Subsequently, whether the cells were dissolved and morphologically changed was observed with a microscope. In a solution mixture of 19% (or less) culture solution/81% 0.1× PBS, adding 10× Lysis Buffer made the boundaries between the cells obscure. This made it possible to determine that dissolving occurred. Ina solution mixture of 25% culture solution/75% 0.1× PBS, adding 10× Lysis Buffer made the cells themselves swell or the cell membranes obscure. This made it possible to confirm that the cells partly became dissolved. However, the nuclei of the cells were left undissolved. The cell in a 100% culture solution showed no morphological change even upon addition of 10× Lysis Buffer. This indicated that cell dissolution was hindered. These results indicated that, in order to efficiently perform cell dissolution, PBS(-) was more preferable than the culture solution, and the ratio of a brought culture solution, if the culture solution was brought, it was preferably restricted to 20% or less of the entire solution.

Next, the influences of PBS (−) on gene expression were examined. Mouse group 2 innate lymphoid cells activated in advance by being stimulated by IL-2/IL-33 were prepared. Each of the mouse group 2 innate lymphoid cells was then suspended in a culture solution or PBS (−). Thereafter, 10 cells (M series) and 10 cells (P series) were manually suctioned from the culture solution and PBS (−), respectively, together with a minute amount of external solution, on a cell-by-cell basis with a pneumatic microinjector (IM-11-2 available from Narishige Group) equipped with a glass capillary having an inner diameter of 15 μm (L-Tip 15 μm 60° 15 mm available from YODAKA GIKEN K.K.) and an electrical manipulator (electrical micromanipulator TransferMan NK2 available from Eppendorf AG), and were discharged into 4 μL of RNase-free water (Nacalai tesque, 06442-95) dispensed in a 0.2 ml PCR tube with a dome cap. After the cells were discharged, the cap was quickly closed, and spinning down was performed by a tabletop microcentrifuge (PMC-060 available from TOMY SEIKO CO., LTD.). Thereafter, the cells were rapidly frozen in liquid nitrogen and preserved at −80° C. Subsequently, cDNA was amplified in accordance with a protocol recommended for SMART-See v4 3' DE Kit. More specifically, the frozen cells were melted on ice, and 6.5 of Master mix (a solution obtained by diluting 10× Lysis Buffer, RNase Inhibitor, Nuclease-free water, and ERCC RNA Spike-In Mix (4456740 available from Thermo Fisher Scientific) contained in the kit with Nuclease-free water by 1,875,000 times and mixing the resultant solutions at 19:1:95:15 (v/v)) was added to each cell. Each cell was left to stand at room temperature for 5 minutes, and Oligo dT In-line 1-12 primer contained in the kit was added to the cell in 1 μL. After thermal denaturation at 72° C. for 3 minutes, each cell was transported onto ice. After the elapse of 2 minutes, 7.5 μL of a solution obtained by mixing 5× Ultra Low First-Strand Buffer, SMART-Seq v4 Oligonucleotide, RNase Inhibitor, and SMARTScribe Reverse Transcriptase in the kit at 8:2:1:4 (v/v) was added to the cell. Reverse transcription was then performed at 42° C. for 90 minutes, and thermal denaturation was performed at 70° C. for 10 minutes. The resultant cell was preserved at 4° C. Subsequently, 30 μL of a solution obtained by mixing 2× SeqAmp PCR Buffer, PCR Primer II A, SeqAmp DNA Polymerase, and Nuclease-free water at 25:1:1:3 (v/v) was added to the cell, and thermal denaturation was performed at 95° C. for 1 minute. The cell was amplified under the condition of repeating three steps, including thermal denaturation at 98° C. for 10 seconds, annealing at 65° C. for 30 seconds, and synthesis at 68° C. for 3 minutes, 18 times. Finally, an elongation reaction was performed at 72° C. for 10 minutes.

The obtained amplified product was dispensed in 1 μL into different PCR tubes, and was diluted with Nuclease-free water 160 times. Of the resultant solution, 1 μL of solution as a template was subjected to quantitative PCR by using StepOnePlus Real-Time PCR Systems available from Applied Biosystems in accordance with the manual for TaqMan Fast Universal PCR Master Mix. The quantitative values Ct of each cell and each gene were calculated by software (StepOne software available from Applied Biosystems) attached to an apparatus. The Gapdh, Rplp0, IL13, and IL5 mRNA expression levels of the respective cells were compared in terms of the number of copies converted from the Ct values of ERCC-00130, ERCC-00136, and ERCC-00131 mRNA in ERCC RNA Spike-In Mix, assuming that the amplification efficiency is the same for the cells.

Figure 9:
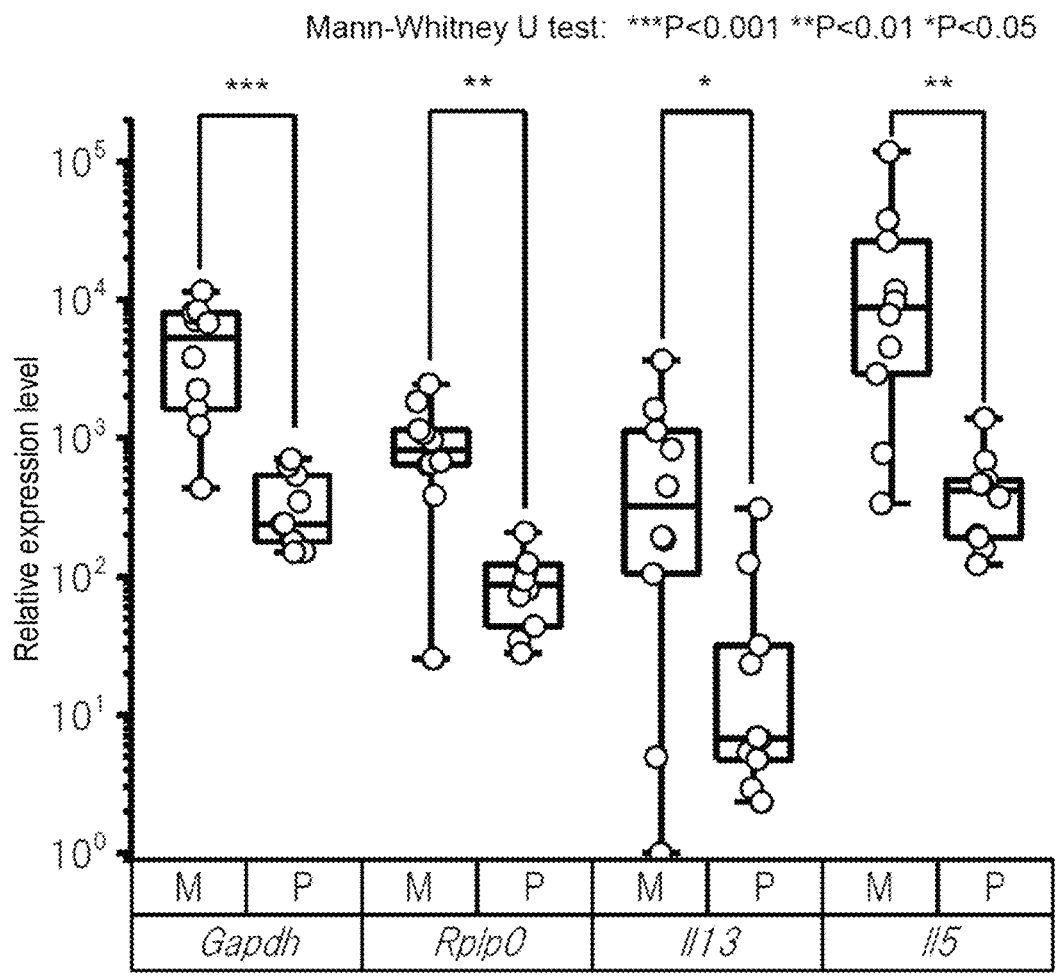
FIG. 9 is a box plots showing the mRNA expression levels of Gapdh, Rplp0, IL13, and IL5 in each mouse group 2 innate lymphoid cell recovered from suspension in a culture medium (M series) and in PBS (P series) after activated by IL-2/IL-33 stimulus.

FIG. 9 shows the results. FIG. 9 is a bar graph showing, as relative expression levels, the numbers of copies converted from the Ct values of ERCC RNA Spike-In concerning the cells (M series) recovered from the medium and the cells (P series) recovered from PBS. It was found that the gene expression levels of the cells recovered from the medium were higher by 10 times or more. A recovery system using a glass capillary used in this study did not allow quantitative evaluation of the brought amount of the medium. This led to concern about a deterioration in each type of gene expression due to inhibition of cell dissolution. In general, however, the gene expression of cells recovered from a culture solution was higher than that of cells recovered from PBS (−). This indicated that, in the recovery system using the glass capillary used in this study, the brought amount of the medium was sufficiently small. In addition, the gene expression levels of cells recovered from PBS (−) were lower by an order of magnitude than those of cells recovered from a culture solution. This indicated that since, for example, the act of replacing a cell external solution with PBS (−) would reduce poly A RNA itself in the cell or would make transition to a state in which poly A RNA could not be amplified as cDNA, the gene expression information of each cell in an activated state was not accurately reflected as a cDNA amount. These results indicated that, in order to measure the activation of a cell, recovering the cell at the time point after the elapse of the time Δd, and obtaining gene expression information reflecting activation information in the cell, it was preferable to recover the cell together with culture solution in an amount minute enough not to influence the subsequent analysis step without replacing a cell external solution and to fix the intracellular gene expression information by freezing or the like as quickly as possible.

Example 6

Example 6 exemplifies a technique of chronologically measuring changes in the states of live cells, recovering the cells on a cell-by-cell basis at the elapse of a preset time Δt, performing exhaustive gene expression analysis such as next-generation sequencing analysis of the poly A RNA expression level held by the cell, and detecting a Δt-specific expressed gene. This Example adopted "cell secretion" as an indicator of a change in cell state of a live cell as in Example 1, and used "single-cell secretion measurement" as an indicator measurement method.

This Example measured the secretion response of IL-13 against IL-33/IL-2/TSLP stimulus on human peripheral blood group 2 innate lymphoid cells (ILC2s), frozen/fixed one cell in one specimen after the elapse of 2.4 hours since the start time point of secretion, an IL-13 secretion negative cell (one cell in four specimens) after the elapse of 120 hours since application of stimulus, and IL-13 secretion positive cells (a plurality of cells from eight cells to 32 cells in three specimens) immediately after recovery, and performed gene expression level analysis of each of the eight specimens by next-generation sequencing. Each step will be described in detail below.

ILC2s from 20 mL healthy human peripheral blood was purified and harvested in a culture solution (RPMI1640 medium, 1×MEM NON-ESSENTIAL AMINO ACID SOLUTION, 10 mM HEPES, 1 mM Sodium Pyruvate, 100 U/ml Penicillin, 100 μg/ml Streptmycin, 55 μm 2-Mercaptoethanol, 50 ng/ml gentamicin sulfate, 10 ng/mL Recombinant Human IL-2 protein (Imunace 35, 087-03356 available from SHIONOGI & CO., LTD.), 10% FCS).

A concave well array chip used in the measurement was prepared by the same technique as in Example 1. Note, however, that the shape and size of each concave well were 80 μm square and 80 μm deep. Anti-human IL-13 capture antibody (Cat #MAB213 available from R&D Systems) was solid-phased on the glass bottom surface of each concave well. ILC2 cells were introduced into the concave well array chip by about 400 to 600 per 1,000 concave wells, and were randomly arranged on a cell-by-cell basis in each one concave well by centrifugal sedimentation at 100 xg for 30 seconds. Cells outside the concave wells were removed by medium replacement. Anti-human IL-13 detection antibody (Cat #BAF213 available from R&D Systems and CF660R Streptavidin, Cat #29040 available from Biotium) fluorescence-labeled via avidin-biotin was added to the observation medium at a final concentration of 30 nM. Measurement was performed with an electrical inverted microscope system (ECLIPSE Ti-E available from Nikon Corporation) including a total internal reflection fluorescence. Imaging was performed with the digital CMOS camera (ORCA-Flash4.0 V2 (C11440-22CU) available from Hamamatsu Photonics K.K.) mounted in the above system. After the concave well array chip was installed, human IL-33/IL-2/TSLP (Recombinant Human IL-33 Protein, Cat #3625-IL/CF available from R&D Systems, Imunace 35, 087-03356 available from SHIONOGI CO., LTD., Recombinant Human TSLP Protein, 1398-TS/CF available from R&D Systems) were added to the cells at final concentrations of 50 ng/mL, 20 U/mL, and 50 ng/mL, respectively.

Figure 10:
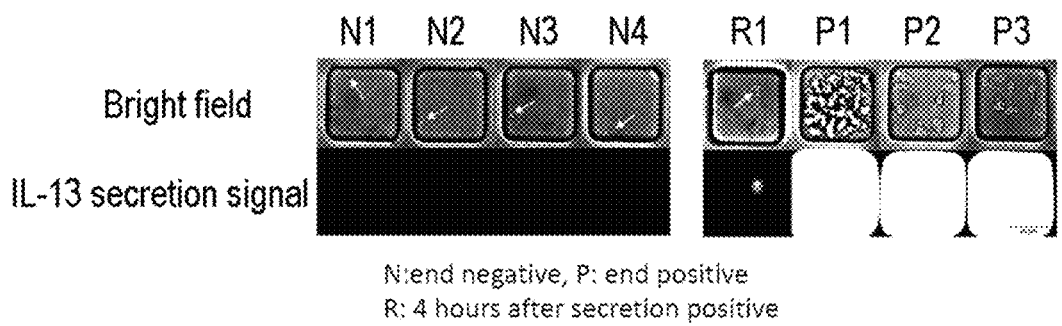
FIG. 10 shows the bright fields and IL-13 secretion fluorescent images of samples obtained by real-time recovery (recovery 2 hours after the start time point of secretion) of human peripheral blood group 2 innate lymphoid cells (ILC2s) activated by IL-33/IL-2/TSLP stimulus or collective recovery (recovery 80 hours after application of stimulus) of them at the end point of measurement.
Figure 11:
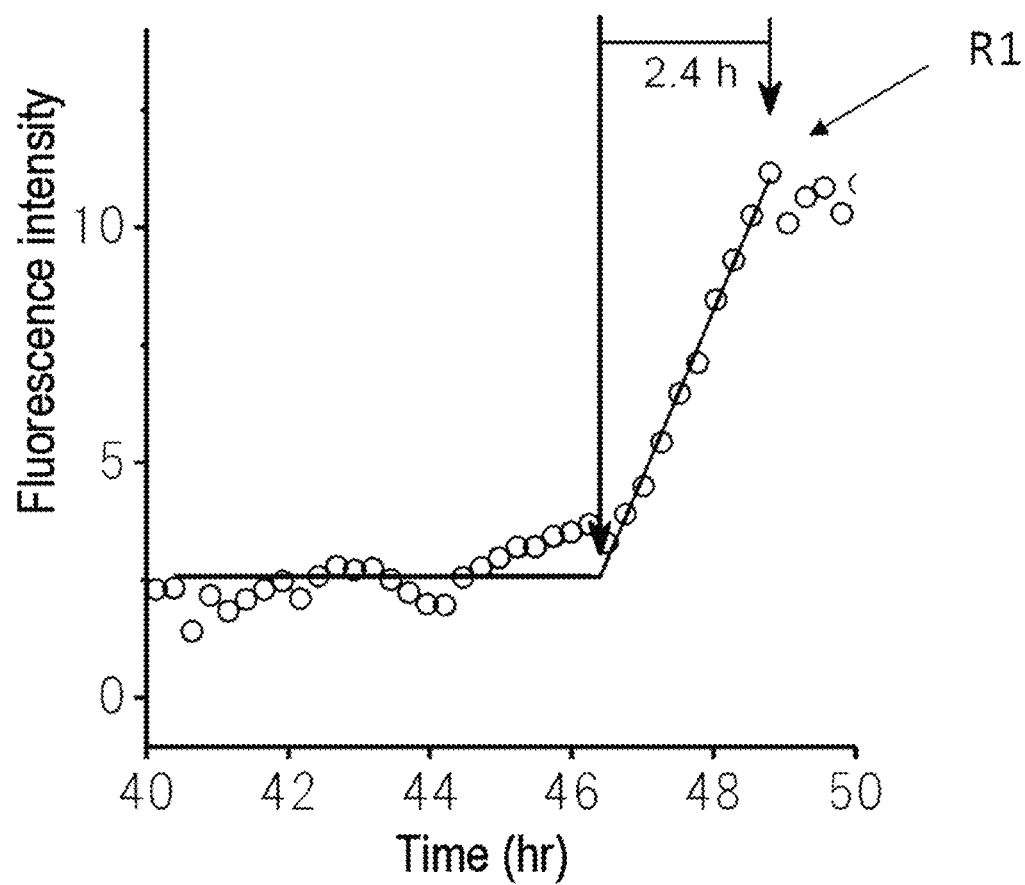
FIG. 11 is a representative graph showing the result obtained by chronologically measuring the fluorescence intensities of IL-13 secretion signals of a cell recovered in real time, which was human peripheral blood group 2 innate lymphoid cells (ILC2s) activated by IL-33/IL-2/TSLP stimulus.
Figure 12:
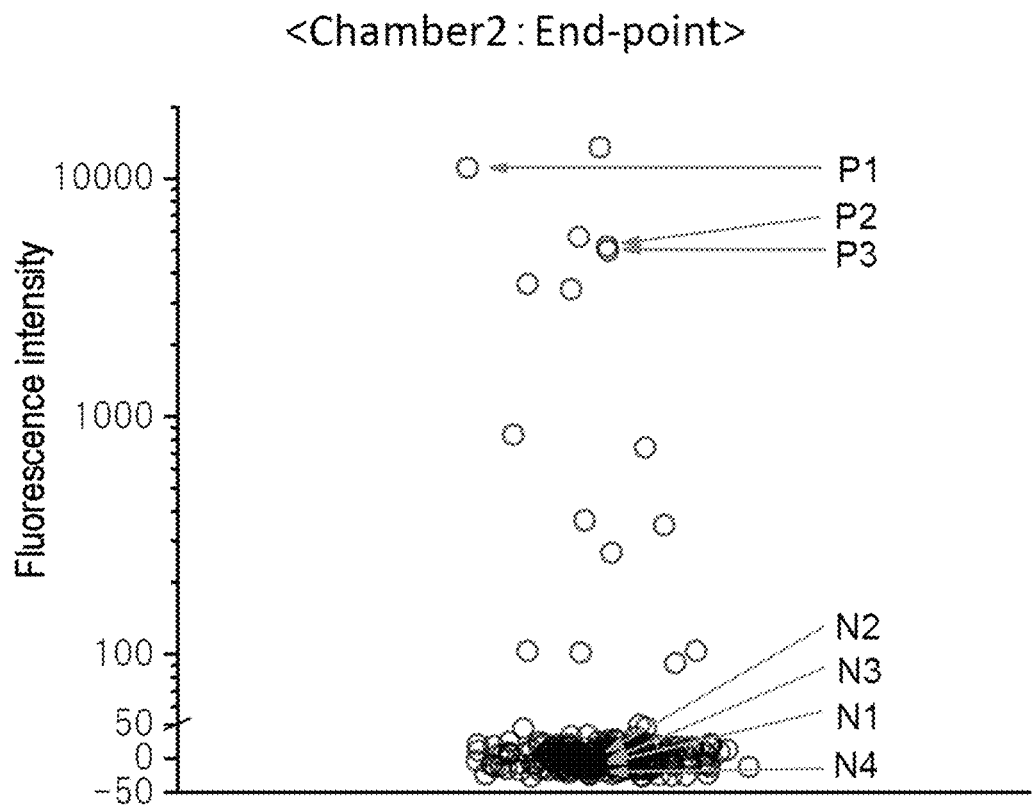
FIG. 12 is a graph showing the result at the end-point in data obtained by chronologically measuring the fluorescence intensities of IL-13 secretion signals of cells collectively recovered at the end point of measurement, which were human peripheral blood group 2 innate lymphoid cells (ILC2s) activated by IL-33/IL-2/TSLP stimulus.

ILC2 cells were activated by stimulation of IL-33/IL-2/TSLP by using the start of IL-13 secretion as an indicator as in Example 1. The secretion of IL-13 was started in real time in accordance with the flowchart of FIG. 2 as in Example 1. Note, however, that since it was expected from preliminary studies that the activation ratio of human ILC2s to that of mouse group 2 innate lymphoid cells was low, the measurement time intervals and the number of measurement concave wells were increased to increase the number of activated cells to be detected. More specifically, IL-13 secretion from one of 196 cells contained in 636 concave array regions was continuously measured at time intervals of 15 minutes for 80 hours. In determining the start time point of secretion from a cell, wells containing no cell were designated in advance, and the value obtained by adding a standard deviation to the average fluorescence intensity of the designated wells was used as a threshold. Each cell determined as positive in secretion determination was assigned with the immediately preceding imaging time point (imaging immediately before imaging used for secretion determination) as the start time point of secretion, and each cell was recovered in real time at the time point after the elapse of 2 hours since the start time point of secretion (upper section of FIG. 10: bright fields, lower section of FIG. 10: IL-13 secretion signal fluorescent images). Note, however, that when a phase transition time point was calculated by linear regression analysis on luminance data before and after the start of secretion in detailed analysis from measurement data after real-time recovery, an actual elapse time Δt from the start of secretion was 2.4 hours (FIG. 11). In this recovery, each cell was manually suctioned, together with a small amount of each medium, under microscope observation, with a pneumatic microinjector (IM-11-2 available from Narishige Group) equipped with a glass capillary having an inner diameter of 15 μm (L-Tip 15 μm 60° 15 mm available from YODAKA GIKEN K.K.) and an electrical manipulator (electrical micromanipulator TransferMan NK2 available from Eppendorf AG), and was discharged into 4 μL RNase-free water (Nacalai tesque, 06442-95) dispensed in a 0.2 ml PCR tube with a dome cap. After the cell was discharged, the cap was quickly closed, and spinning down was performed by a tabletop microcentrifuge (PMC-060 available from TOMY SEIKO CO., LTD.). After the cell suspended solution was dropped onto the PCR tube bottom, the cell was rapidly frozen in liquid nitrogen and preserved at −80° C.

With the above work, one cell was recovered in real time at the elapsed time Δt=2.4 hours, with secretion being an indicator. FIG. 10 shows an example of detailed analysis at the elapsed time Δt which was performed after the end point of measurement/recovery of a cell (R1) recovered in real time. The arrows indicate the start time point of secretion and a recovery point. The signal stopped increasing at the recovery point.

Following the real-time recovery, in comparison with the above operation, secretion negative/secretion positive cells at the end time of measurement, which had no time-dependent information concerning a change in indicator, were recovered (collective recovery at end point of measurement). IL-13 secretion 120 hours after stimulation was measured in concave wells (996) outside the range of the above chronological observation (the bright field images upon final recovery on the upper section of FIG. 10 and the IL-13 secretion signal fluorescent images). As shown in FIG. 10, with regard to IL-13 secretion measurement after the elapse of 120 hours since application of stimulus, secretion signals obtained from 248 concave wells each containing one or more cells were compared, and concave wells with signal values near 0 were determined as concave wells containing secretion negative cells. Of these wells, four concave wells were randomly selected from the concave wells each containing one cell, and the contained cell groups (N1 to N4 in FIG. 10) were recovered by using the above apparatus. In addition, concave wells with fluorescence intensity values of 200 or more, in which clear secretion signals were observed, were determined as secretion positive wells. Three concave wells were randomly selected from these wells, and cells (P1 to P3 in FIG. 10) contained in the selected wells were recovered. The respective concave wells respectively contained 32 cells, 8 cells, and 8 cells, each of which groups was considered to be divided from one cell. These clone cell groups apparently increased in cell body size. This made it difficult to recover the cells with the above glass capillary having an inner diameter of 15 μm. For this reason, recovery was performed with a glass capillary having an inner diameter of 50 μm (L-Tip 50 μm 60° 15 mm available from YODAKA GIKEN K.K.) in the same manner as described above.

ILC2s recovered in real time, with IL-13 secretion being an indicator, and frozen/preserved in the above described manner and ILC2 cells (both secretion negative cells and secretion positive cells) collectively recovered at the end point of measurement were subjected to cDNA preparation using SMART-See v4 Ultra® Low Input RNA Kit for Sequencing. Library preparation for the resultant cells was entrusted to next-generation sequencing contract service (implementation site: Kazusa DNA Research Institute) in Medical & Biological Laboratories Co., Ltd. (MBL), thus performing gene expression level analysis using a next-generation sequencer. A search was made, in obtained Fastq files, for a gene expression pattern specifically appearing in real-time recovery.

The following is a detailed description of cDNA preparation. This operation was basically performed in accordance with moiety protocols of recommended protocols for the above kit. A solution of 1.25 μL, obtained by mixing 10×

Lysis Buffer, RNase Inhibitor, and Nuclease-free water, included in this kit, at 19:1:30 (v/v), was mixed with a solution obtained by mixing SMART-Seq CDS Primer II A with Nuclease-free water, included in the kit, μL by μL, thus obtaining a working solution. After each PCR tube containing ILC2s frozen after being discharged to 4 μL of RNase-free water was taken out from −80° C. to room temperature, 2.25 μL of working solution was immediately added to the tube. After thermal denaturation at 72° C. for 3 minutes, each cell was transported onto ice. After the elapse of 2 minutes, 3.75 μL of a solution obtained by mixing 5× Ultra Low First-Strand Buffer, SMART-Seq v4 Oligonucleotide, RNase Inhibitor, and SMARTScribe Reverse Transcriptase in the kit at 8:2:1:4 (v/v) was added to the cell. Reverse transcription was then performed at 42° C. for 90 minutes, and thermal denaturation was performed at 70° C. for 10 minutes. The resultant cell was preserved at 4° C. Subsequently, 15 μL of a solution obtained by mixing 2× SeqAmp PCR Buffer, PCR Primer II A, SeqAmp DNA Polymerase, and Nuclease-free water, contained in the kit, at 25:1:1:3 (v/v) was added to the cell, and thermal denaturation was performed at 95° C. for 1 minute. Each cell was then amplified under the condition of repeating three steps, including thermal denaturation at 98° C. for 10 seconds, annealing at 65° C. for 30 seconds, and synthesis at 68° C. for 3 minutes, 24 times for R1 and N1 to N4, 18 times for P1, and 20 times for P2 and P3. Finally, an elongation reaction was performed at 72° C. for 10 minutes. After 1 μL of 10× Lysis Buffer in the kit was added to 25 μL of the amplified cDNA product, 50 μL of Agencourt AMPure XP beads (A63881 available from BECKMAN COULTER) returned to room temperature and sufficiently suspended upon addition of 1 μL of 10× Lysis Buffer in the kit was vortexed and suspended to a uniform state. The solution was then left to stand at room temperature for 8 minutes. After spinning down was slightly performed, the resultant solution was transported to a magnetic stand (NGS MagnaStand (YS-Model) 8 Ch for 0.2 mL PCR tube, FG-SSMAG2 available from Nippon Genetics), and was placed for 5 minutes or more until the solution became colorless and transparent. In this state, the supernatant was removed, and 200 μL of 80% ethanol was added to the solution. The solution was then left to stand for 30 seconds, and the supernatant was removed. After 200 μL of 80% ethanol was added to the solution and left to stand for 30 seconds, the supernatant was removed. The tube was then removed from the magnetic stand and slightly spun down. The tube was returned to the magnetic stand and left to stand for 30 seconds. The remaining solution was removed, and the tube was left to stand for several minutes while the cap was open, thus drying the magnetic beads. Elution Buffer of 17 μL included in the kit was added to the tube. The tube was removed from the magnetic stand, and the magnetic beads were sufficiently suspended by tapping. The tube was left to stand at room temperature for 2 minutes. The tube was slightly spun down and returned again to the magnetic stand. The tube was then left to stand for 1 minute or more until the supernatant became colorless and transparent. The colorless, transparent supernatant was transported into a non-suction tube (Treff PCR tube 0.2 mL, 96.10560.9.01, available from TOHO) and preserved by freezing. Each prepared cDNA sample was quantified by using Qubit® dsDNA HS assay kit (Q32851 available from ThermoFisher Scientific), and was adjusted to 10 ng/35 μL by using Elution Buffer contained in SMART-Seq® v4 Ultra® Low Input RNA Kit for Sequencing. Each sample was then sent to Kazusa DNA Research Institute. The request contents were library preparation (KAPA HyperPlus Library Preparation Kit) and 50 bp Single-Read analysis with illumina HiSeq.

Next, a data processing process from Fastq files as contract analysis results will be described.

First, the Fastq files were trimmed by using a quality trimmer of FastQC program (http://www.bioinformatics.babraham.ac.uk/projects/fastqc/). Bases having quality values of less than 20 were removed, and fragment lengths of 30 or less were discarded. The trimmed Fastq files were then mapped into a BAM file by using TopHat ver2.1.0 (https://ccb.jhu.edu/software/tophat/index.shtml). In mapping, NCBI build37.2 was used as an annotation file and reference genome file. FPKM was then calculated from this BAM file by using cufflinks v2.2.1 and used as gene expression level data.

Figure 13:
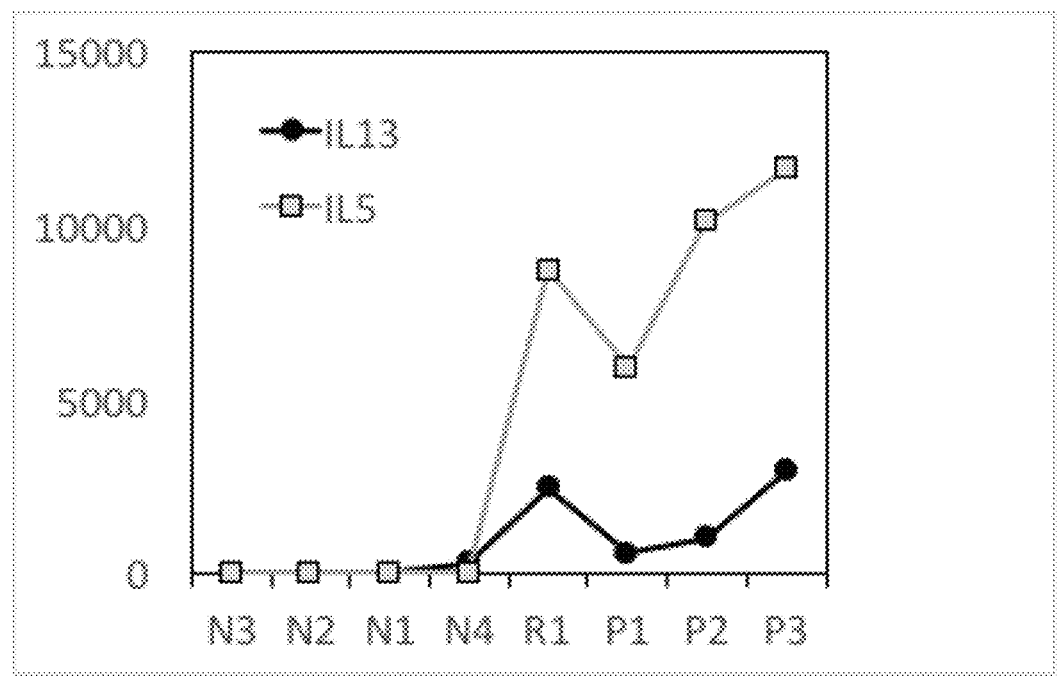
FIG. 13 shows the results (FPKM values) obtained by analyzing, with a next-generation sequencer, the IL-13 and IL-5 mRNA amounts of samples obtained by real-time recovery (recovery 2 hours after the start time point of secretion) of human peripheral blood group 2 innate lymphoid cells (ILC2s) activated by IL-33/IL-2/TSLP stimulus or collective recovery (recovery 80 hours after application of stimulus) of them at the end point of measurement.
Figure 14:
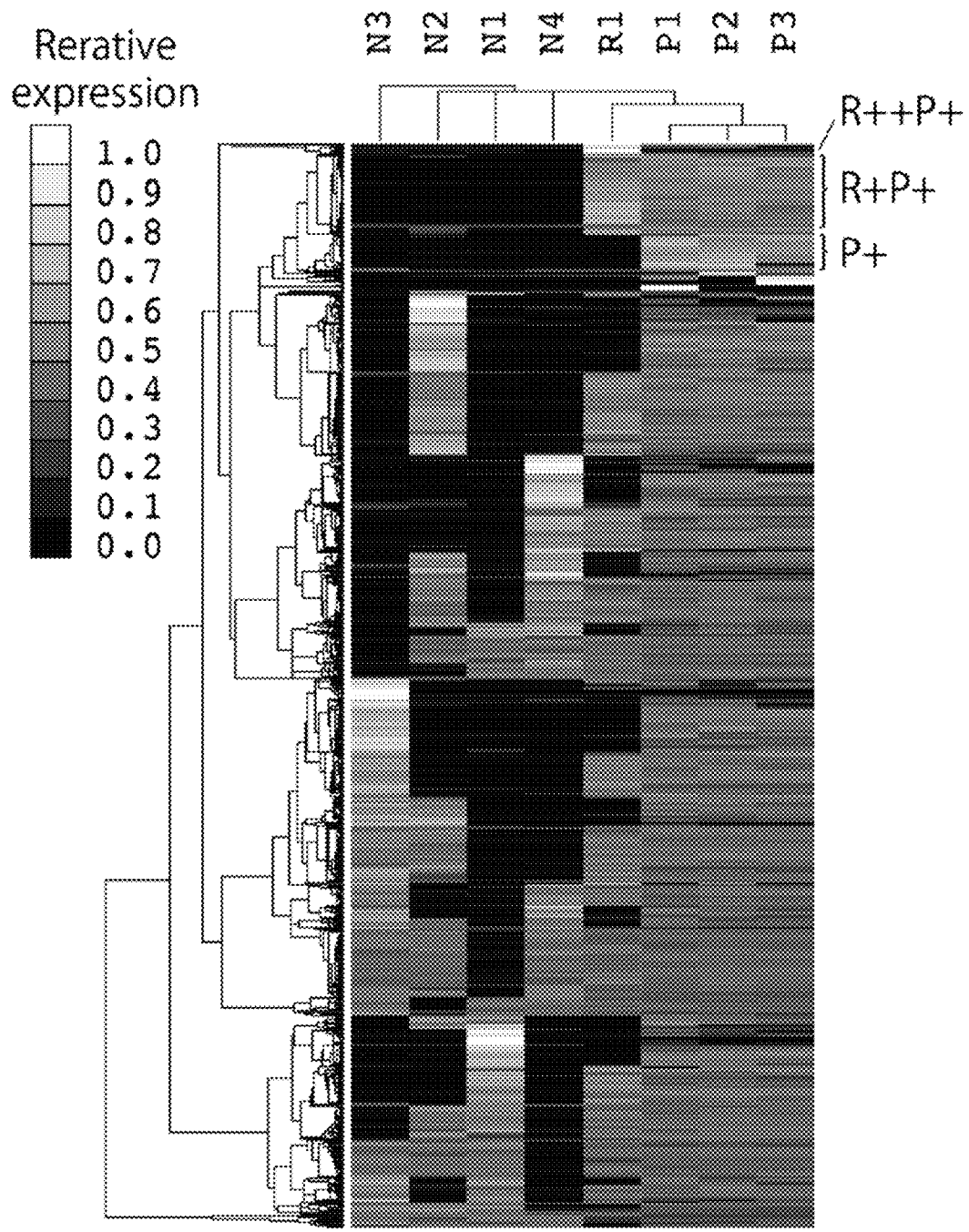
FIG. 14 shows the results obtained by cluster analysis of the FPKM values of all the genes in samples obtained by real-time recovery (recovery 2 hours after the start time point of secretion) of human peripheral blood group 2 innate lymphoid cells (ILC2s) activated by IL-33/IL-2/TSLP stimulus or collective recovery (recovery 80 hours after application of stimulus) of them at the end point of measurement.
Figure 15:
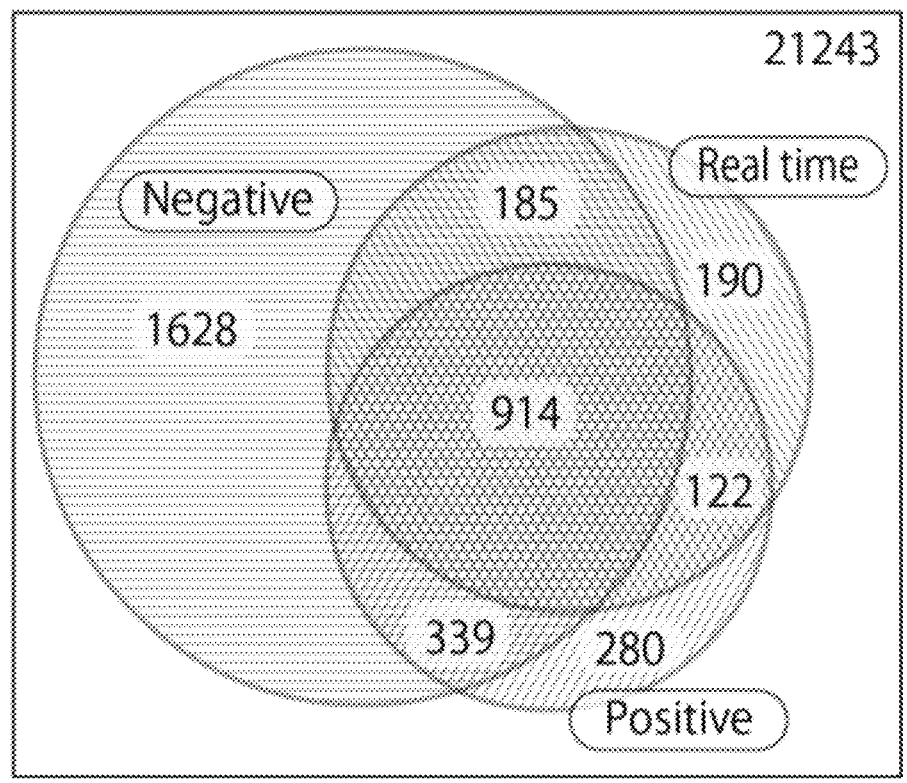
FIG. 15 is a Venn diagram obtained by performing classification thresholding on the FPKM values of all the genes in samples obtained by real-time recovery (recovery 2 hours after the start time point of secretion) of human peripheral blood group 2 innate lymphoid cells (ILC2s) activated by IL-33/IL-2/TSLP stimulus or collective recovery (recovery 80 hours after application of stimulus) of them at the end point of measurement.

Consider FPKM data obtained from N1 to N4, R1, and P1 to P3. First, the FPKM value of the gene IL13 coding for IL-13 protein used as an indicator for activation was compared with the FPKM value of the gene IL5 coding for IL-5 protein known to be secreted from activated ILC2 like IL-13 among the respective samples (FIG. 13). Each of the secretion negative cells (N1 to N3) exhibited a very small value, whereas each of the secretion positive cells (R1 and P1 to P3) exhibited a relatively large value. Accordingly, it was confirmed that the FPKM values obtained by the above procedures reflected intracellular states. Next, the following two types of analyses were conducted on the FPKM values of all the genes. First, a cluster analysis was conducted (FIG. 14). Cluster 3.0 software (http://bonsai.hgc.jp/~mdehoon/software/cluster/software.htm) was used for clustering. A logarithm having 10 as its base, which is obtained by adding 1 to an obtained FPKM value, was used for a cluster analysis. When at least one of the seven samples exhibited a logarithmic value of 2.0 or more and the distance between the maximum value and the minimum value among the seven samples was 1 or more (3, 301 genes among 24, 901 genes), only the corresponding data were regarded as targets and converted into relative values among the respective genes. Similarities were determined based on City-block distances as the distance measures between the samples and Pearson correlation coefficients as the distance measures between the respective genes, and clusters were formed by the centroid method. Detailed study was carried out for each node, of the obtained clusters, which exhibited a correlation coefficient of 0.9 or more. This revealed a cluster (R++P+) in which R1 exhibited a high value and P exhibited a low value, a cluster (R+P+) in which R1 exhibited a high value, and P also exhibited a similarly high value, and a cluster (P+) in which only P exhibited a high value. A study was then conducted, by a binarization method, on whether an expression pattern obtained by real-time recovery exhibited a feature. More specifically, an intermediate expression threshold for FPKM was set to 100, and the determination criteria were whether the FPKM of each gene in R1 exceeded the threshold, and at least one sample of N1 to N4 and P1 to P3 exceeded the threshold. FIG. 15 is a Venn diagram showing the results obtained by classifying all the 24,901 genes based on this determination. As a result, 190 types of genes were classified as exhibiting R1-specific expression values equal to or more than the intermediate value.

Table 1 below provides a summary of the studied relationship between the following two types of classifications.

TABLE 1

|  |  | Cluster Analysis | | | | |
| --- | --- | --- | --- | --- | --- | --- |
|  |  | R++P+ | R+P+ | P+ | Other | Total |
| Binarization Method | R1-specific | 25 | 104 | 0 | 61 | 190 |
|  | Other | 0 | 130 | 88 | 24493 | 24711 |

Of the R1-specific genes obtained by the binarization method, 129 genes were included in cluster R++P+ and cluster R+P+. None of the R1-specific genes obtained by the binarization method were included in cluster P+. That is, secretion start time specific gene groups specified only by real-time recovery were successfully found.

Example 7

Example 7 adopted "morphological change" as an indicator of a change in the cell state of a live cell, and used "time-lapse photography by phase-contrast microscope method" as an indicator measurement method.

This Example exemplifies a method for detecting a transient morphological change characteristic to an induced pluripotent step cell (iPS cell) during long-term culturing in Essential 8 Medium (E8 Medium; A1517001 available from ThermoFisher Scientific).

Figure 16:
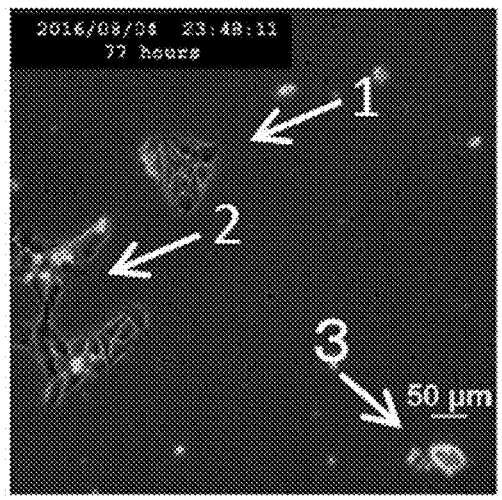
FIG. 16 shows a phase contrast image (upper image) obtained when human induced pluripotent stem cell IM-E1-5 lines were cultured in E8 medium, an image (intermediate image) obtained when cell regions were identified by binarizing the phase contrast image upon setting a threshold, and a feature amount image (lower image) obtained by conducting edges detection on the phase contrast image.
Figure 16:
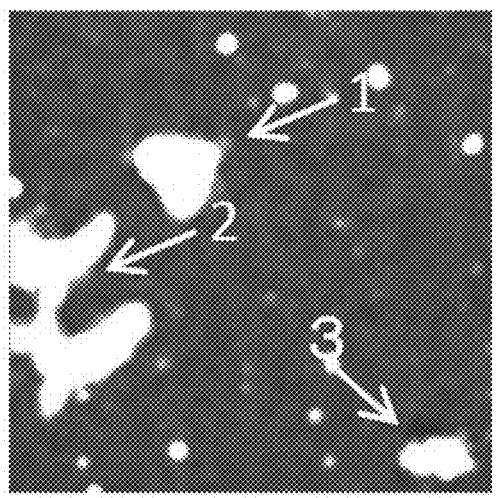
Figure 16:
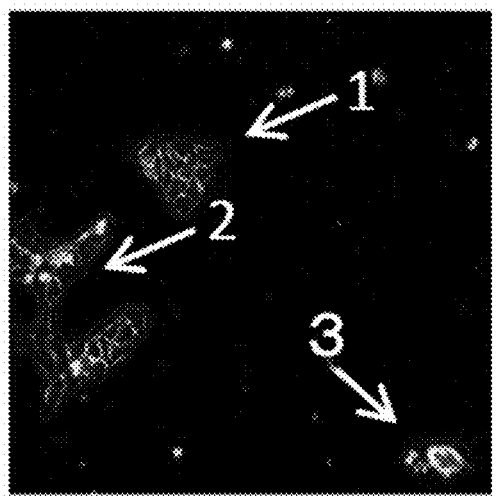

The iPS cells used in this Example were IM-E1-5 lines (Stem Cells Transl. Med., 4, 468-75, 2015). The cells were seeded in a 6-well plate coated with Geltrex® LDEV-Free hESC-qualified Reduced Growth Factor Basement Membrane Matrix (A1413301 available from ThermoFisher Scientific) and cultured in E8 Medium. FIG. 16 shows phase difference images of the cells observed with a 20× objective lens (S Plan Fluor ELWD 20× Ph1 available from Nikon Corporation). A typical morphology is similar to an epithelial cell with a slightly high degree of stretching. In each obtained image, the cells adhered to each other and stretched over several tens of pm (indicated by arrows 1 and 2 in FIG. 16). However, time-lapse photography performed once per 10 minutes showed a phenomenon in which in each colony originating from one cell to several loosen and dispersed cells, the colony swelled in a dome shape around 48 hours after the start of culturing, and a morphological change that made the boundaries between the respective cells obscure transiently occurred for only several tens of minutes. Accordingly, it was studied whether this transient morphology was able to be quickly detected by image processing so as to use the detected morphology as an indicator of a change in cell state.

Figure 17:
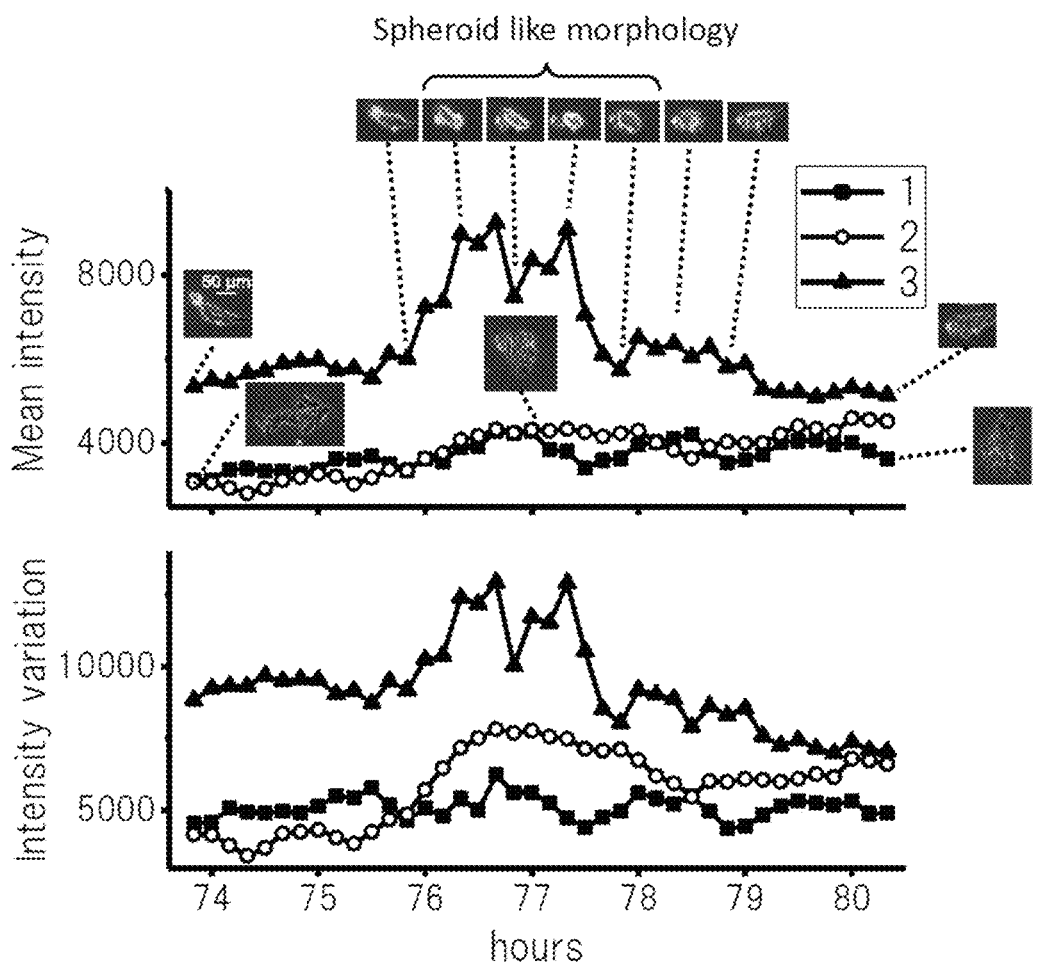
FIG. 17 shows graphs plotted signal changes in a feature amount image acquired during culturing of human induced pluripotent stem cell IM-E1-5 lines using E8 medium. The upper graph shows changes in average signal intensity in each cell region of the feature amount image. The lower graph shows changes in signal variance.

In order to quantitatively extract a feature of the morphological change, image processing using ImageJ was performed with respect to the phase difference image of the cells. More specifically, Edges Detection was performed for the image obtained by subtracting the background from the original image (feature amount image). Aside from this, Detect Peak was performed for the image obtained by subtracting the background from the original image, and a low pass filter was then applied to the resultant image. The resultant image was then binarized with a threshold that was able to extract the existing ranges of colonies formed by cells, thereby identifying cell regions. Signal changes of the above feature amount image in the respective cell regions were measured, and the result was plotted. Referring to FIG. 17, temporal variations in feature amounts quantified with respect to the cell colonies specified by arrows 1 to 3 in FIG. 16 were plotted. In this case, average signal intensity variations in the respective cell region of the feature amount image (the upper section of FIG. 17) and signal variance variations (the lower section of FIG. 17) were quantified. In either case, while the variations in colonies 1 and 2 were small, the intensity in colony 3 abruptly increased at the elapse of about 76 hours and returned to the value before the increase by 78 hours although they greatly varied. FIG. 17 shows the morphologies of the respective colonies at the time points indicated by the broken lines in the graph. The signal increase in colony 3 at the elapse of about 76 hours is considered to follow a phenomenon in which the thickening of the colony (detected by the halo (blurring of light) around each cell on the phase difference image) and the boundaries between the respective cells included in the colony become obscure. The contour of each cell included in the colony gradually became clear at the elapse of about 78 hours, and the signal intensity was also stabilized following this phenomenon. In contrast to this, almost no signal change occurred in colonies 1 and 2 on the phase difference image. As described above, the morphological changes of the iPS cell colonies, which transiently occurred for several tens of minutes over several days, were successfully quantified as feature amounts by simple image processing.

As described above, for example, using a spheroid like morphological change of each iPS cell colony as an indicator enables recovery of an iPS cell after the elapse of a predetermined time since a change in the indicator.

In this Example, morphological information as a luminance value is quantified. However, various other image feature amount detection methods can be used. For example, it is possible to adopt an information amount suitable for each cell morphological change from feature amounts that can be quantified by image analysis, including the area of a colony, a peripheral shape such as a roundness, an intracolony intensity distribution, the length of a linear shape pattern that can be detected in the colony, and the number of linear shape patterns. In addition, it is possible to perform detection based on image classification using machine learning and deep learning by preparing a teacher image library having desired morphological information and a teacher image library for comparison in advance.

Example 8

Example 8 adopted "cell activation indicator" as an indicator of a change in the cell state of a live cell and used "time-lapse photography by live cell imaging" as an indicator measurement method.

Currently, there are many types of cell activation indicators that can be used for live cell imaging. A cell activation indicator is a low-molecular compound or genetically altered protein that does not inhibit all types of cell activation or has an inhibiting effect small enough not to influence the examination of target cell activation, and allows detection of the degree of target cell activation in the form of a change in the intensity of fluorescence or chemiluminescence or a change in intracellular location (see, for example, "Fluorescence Imaging" edited by Tokuko Haraguchi, Hiroshi Kimura, and Yasushi Hiraoka, Kyoritsu Shuppan).

In this Example, controlled cell death as a typical type of cell activation was detected by using a cell death detection low-molecular fluorescence indicator, SYTOX® Orange Nucleic Acid Stain (S11368 available from ThermoFisher Scientific). In general, as cell death progresses, intracellular information (DNA, RAN, proteins, and the like) is degraded. It is therefore expected that intracellular information will greatly vary after the elapse of Δt since the detection of cell death. SYTOX Orange permeates a cell accompanying opening of the cell membrane as one process of cell death, and combines with nuclear DNA to generate fluorescence. This makes it possible to detect cell death as an increase in fluorescence signal.

A cell used in this Example is iBMM, i.e., mouse bone marrow-derived macrophage cell line immortalized by gene transfer (J. Biol. Chem., 286, 9587-97, 2011).

Figure 18:
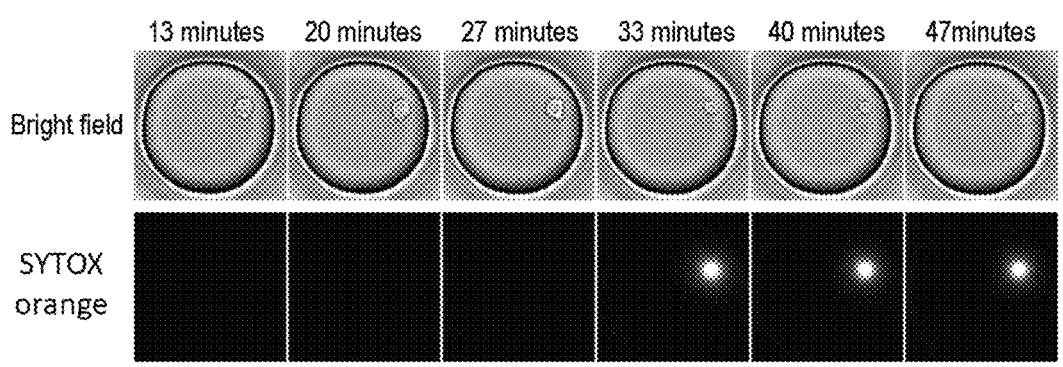
FIG. 18 shows the results obtained by chronologically observing the morphological changes of cells in bright fields and SYTOX orange fluorescence of mouse bone marrow-derived macrophage cell lines iBMM stimulated with poly (dA·dT) DNA.
Figure 19:
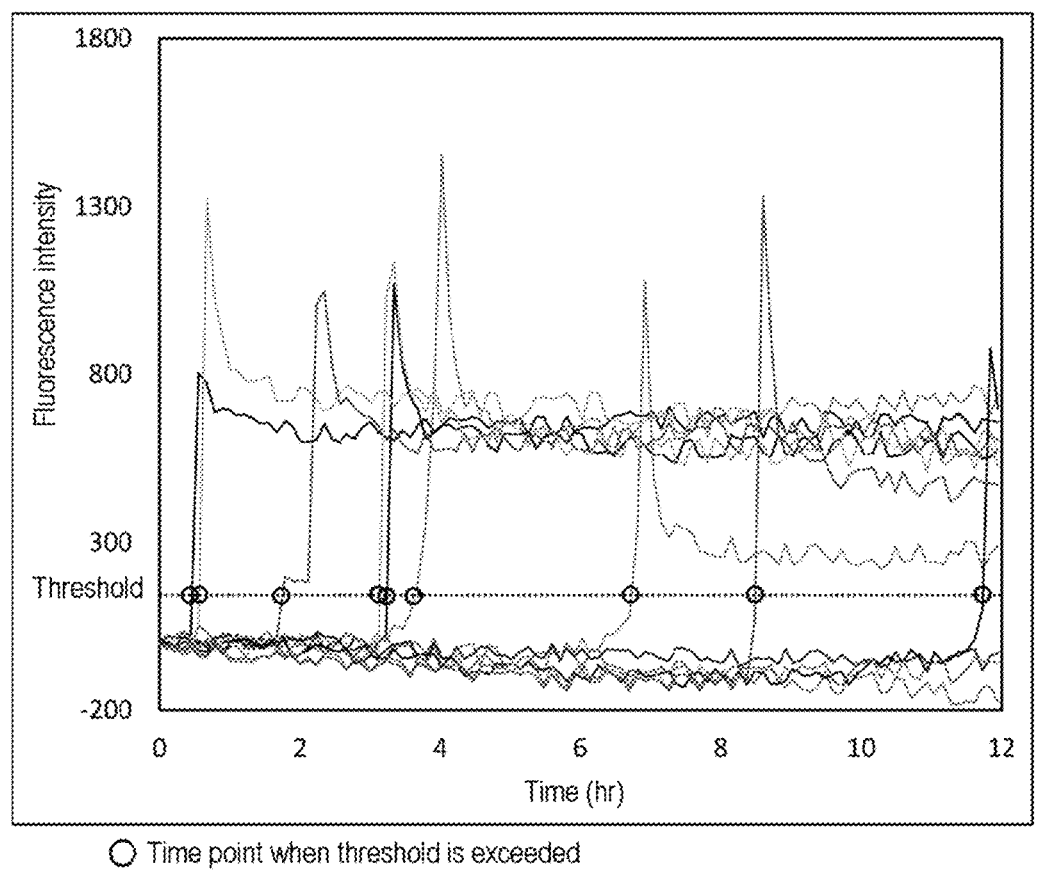
FIG. 19 is a graph obtained by plotting temporal changes in the SYTOX orange fluorescence intensities of mouse bone marrow-derived macrophage cell lines iBMM stimulated with poly(dA·dT) DNA.

A cell was introduced into a 80-μm diameter open well array chip. While 0.01 μM of SYTOX orange was added to a medium, time-lapse observation of the cell was performed every 7 minutes (FIG. 18). When poly(dA·dT) DNA (Poly (deoxyadenylic-thymidylic) acid sodium salt, double-stranded alternating copolymer, P0883-10UN available from SIGMA) was transfected at T=0, abrupt increases in fluorescence intensity were observed in a wide range over several tens of minutes to 10 hours or more after stimulation. That is, it was observed that cell deaths occurred at various timings. Plotting temporal changes in SYTOX Orange fluorescence intensity in cells (FIG. 19) reveals that signals rise very steeply. Providing a threshold for discrimination from background light and identifying points exceeding the threshold made it possible to detect the opening timing of the cell membrane accompanying cell death in real time. Recovering a cell with this timing being an indicator in the same manner as in the above Examples can contribute to gene expression analysis and the like.

The invention claimed is:

1. A cell recovery method for recovering a specific cell from a cell group including a plurality of cells having cell information that changes over time on a cell-by-cell basis, comprising:
   (a) a step of detecting or measuring a desired indicator in each cell of the cell group along a time axis on a cell-by cell basis, wherein the indicator is selected from the group comprising a secreted protein from a cell, morphology of a cell, cell activation, protein expression or mRNA transcription;
   (b) a step of comparing a detected value or a measured value obtained in the step (a) with a preset threshold, and determining the cell having the detected or measured value that is exceeding the threshold as a cell to be recovered from the cell group on a cell-by-cell basis;
   (c) a step of comparing a detected value or a measured value having time axis information obtained in the step (a) with a preset threshold and specifying a time point when the threshold is exceeded on a cell-by-cell basis; and
   (d) a step of recovering the cell that is determined as a cell to be to be recovered in the step (b) on a cell-by-cell basis, wherein the cell is recovered at a time point after elapse of a preset time since the time point when the threshold is exceeded that is specified in the step (c).

2. The cell recovery method according to claim 1, further comprising, after the step (b),
   (c) a step of correcting the time point when the threshold is exceeded based on information of the chronologically acquired indicator with respect to a recovered cell, and calculating an elapsed time from the corrected time point when the threshold is exceeded.

3. The cell recovery method according to claim 1, wherein each of the steps is performed on an array chip including a plurality of wells each containing one cell.

4. The cell recovery method according to claim 1, wherein the steps (a), (b), (c) and (d) are repeated multiple times to recover a plurality of specific cells.

5. The cell recovery method according to claim 4, wherein not less than two different times each are set as the preset time to recover specific cells in at least two groups of different states.

6. The cell recovery method according to claim 1, wherein the step (b) comprises a step of fixing a cell at a time point after elapse of a preset time since the time point when the threshold is exceeded that is specified in the step (c) and recovering the fixed cell.

7. The cell recovery method according to claim 1, wherein the step (d) comprises a step of transporting the recovered cell to a fixative solution or a culture solution.

8. The cell recovery method according to claim 1, wherein detection or measurement of the indicator is performed by a sandwich immunoassay using the evanescent light as an excitation light generated only near a well bottom surface.

9. A method for processing a cell recovered by a method according to claim 1 for cell information analysis, wherein the step (d) comprises a step of transporting a cell in a culture solution into purified water or inorganic saline solution, and recovering the cell together with the culture solution such that a ratio of the culture solution to whole purified water or whole inorganic saline solution becomes not more than 20% (v/v), and
   the method further comprises a step of fixing a recovered cell in the purified water or the inorganic saline solution.

10. A cell analysis method comprising a step of analyzing a cell recovered by a method according to claim 1.

11. A system for recovering a specific cell on a cell-by-cell basis from a cell group including a plurality of cells having cell information that changes over time,
   comprising a detection unit configured to detect or measure a desired indicator in each cell of the cell group along a time axis on a cell-by-cell basis, wherein the indicator is selected from the group comprising a secreted protein from a cell, morphology of a cell, cell activation, protein expression or mRNA transcription,
   an analyzing unit configured to specify
      a) a cell having the detected or measured value that is exceeding the threshold by comparing a detected value or a measured value with a preset threshold,
      b) a time point when the threshold is exceeded by comparing a detected value or a measured value having time axis information with a preset threshold, and
      c) a time point after elapse of a preset time since a time point when the threshold is exceeded on a cell-by-cell basis, and
   a recovering unit configured to recover a cell having the detected or measured value that is exceeding the threshold at a time point after elapse of a preset time since a time point when the threshold is exceeded on a cell-by-cell basis.

12. A cell analysis method comprising a step of analyzing cell information of a cell prepared by a method according to claim 9.

* * * * *